US005789608A

United States Patent [19]
Glazier

[11] Patent Number: 5,789,608
[45] Date of Patent: Aug. 4, 1998

[54] PHOSPHORUS PRODRUGS

[75] Inventor: Arnold Glazier, Newton, Mass.

[73] Assignee: Drug Innovation and Design, Inc., Needham, Mass.

[21] Appl. No.: 763,412

[22] Filed: Dec. 11, 1996

Related U.S. Application Data

[60] Division of Ser. No. 310,972, Sep. 23, 1994, Pat. No. 5,627,165, which is a continuation-in-part of Ser. No. 714,130, Jun. 11, 1991, abandoned, which is a continuation-in-part of Ser. No. 537,332, Jun. 13, 1990, abandoned.

[51] Int. Cl.$^6$ .................................................. C07D 413/00
[52] U.S. Cl. .............................. 554/116; 560/8; 560/76; 568/8; 568/13; 568/14
[58] Field of Search ............................ 554/116; 560/8, 560/76; 568/8, 13, 14

[56] References Cited

U.S. PATENT DOCUMENTS

| | | | |
|---|---|---|---|
| 3,160,638 | 12/1964 | Folkers et al. | 260/345.5 |
| 4,468,384 | 8/1984 | Bardos et al. | 514/49 |
| 4,990,499 | 2/1991 | Gopta et al. | 514/49 |
| 5,274,162 | 12/1993 | Glazier | 558/166 |
| 5,627,165 | 5/1997 | Glazier | 514/75 |

FOREIGN PATENT DOCUMENTS

| | | |
|---|---|---|
| 0331032 A1 | 9/1989 | European Pat. Off. |
| 0338372 A2 | 10/1989 | European Pat. Off. |
| 0360609 A2 | 3/1990 | European Pat. Off. |
| WO91/19721 | 12/1991 | WIPO |

OTHER PUBLICATIONS

Mitchell, Anthony G. et al., "Bioreversible Protection for the Phospho Group: Bioactivation of the Di(4–acyloxybenzyl) and Mono(4–acyloxybenzyl) Phosphoesters of Methylphosphonate and Phosphonacetate," *J. Chem. Soc. Perkin Trans.1*:2345–2353 (1992).

Thomson, William et al., "Synthesis, Bioactivation and Anti–HIV Activity of the Bis(4–acyloxybenzyl) and Mono(4–acyloxybenzyl) Esters of the 5'–Monophosphate of AZT," *J. Chem. Soc. Perkin Trans.* 1:1239–1245 (1993).

Mitchell, Antony G. et al., "Prodrugs of Phosphonoformate: The Effect of para–Substituents on the Products, Kinetics and Mechanism of Hydrolysis of Dibenzyl Methoxycarbonylphosphonate," *J. Chem. Soc. Perkin Trans.* 2:1145–1150 (1992).

Freeman, Sally et al., "Bioreversible Protection for the Phospho Group: Chemical Stability and Bioactivation of Di(4–acetoxy–benzyl) Methylphosphonate with Carboxyesterase," *J. Chem. Soc., Chem. Commun.*:875–877 (1991).

Nakamura, Tetsuya and Kijima, Shizumasa, "Studies on Tocopherol Derivatives. II. Synthesis of Phosphomethyl Tocopheryl Acetates," *Chem. Pharm. Bull.* 20(4):794–799 (1972).

Iyer, Radhakrishnan P. et al., "Synthesis of Acyloxyalkyl Acylphosphonates as Potential Prodrugs of the Antiviral, Trisodium Phosphonoformate (Foscarnet Sodium)," *Tetrahedron Letters*, 30(51):7141–7144 (1989).

Sastry, Jagannadha K. et al., "Membrane–Permeable Dideoxyuridine 5'–Monophosphate Analogue Inhibits Human Immunodeficiency Virus Infection," *Molecular Pharmacology*, 41:441–445 (1992).

Farquhar, David et al., "Biologically Reversible Phosphate–Protective Groups," *J. Pharm. Sci.*, 72(3):324–325 (1983).

Srivastva, Devendra N. and Farquhar, David, "Bioreversible Phosphate Protective Groups: Synthesis and Stability of Model Acyloxymethyl Phosphates," *Bioorganic Chemistry*, 12:118–129 (1984).

Wakselman, Michel and Vilkas, Michel, "Réaction des o–et p–hydroxyméthyl–phénols avec les halogénures d'acétyle. Préparation d'acétates d'halométhyl–phénols," *C.R. Acad. Sc. Paris*, t. 259:4292–4294 (1964) Group 8; with English Abstract, *Chemical Abstract* CA62:11730g.

Starrett, John E., Jr. et al., "Synthesis and Invitro Evaluation of a Phosphonate Prodrug Bis(pivaloyloxymethyl) 9–(2–phos–phonylmethoxyethyl)adenine," *Antiviral Research*, 19:267–273 (1992).

*Primary Examiner*—James O. Wilson
*Attorney, Agent, or Firm*—Hamilton, Brook, Smith & Reynolds, P.C.

[57] ABSTRACT

The composition and methods of synthesis of phosphorus prodrugs are described. These methods can be used to convert negatively charged phosphorous bearing drugs into neutrally charged; lipid soluble prodrugs which are able to passively diffuse into cells and into tissues in vivo. Prodrugs for a variety of antiviral and anti-leukemic agents are described.

3 Claims, 9 Drawing Sheets

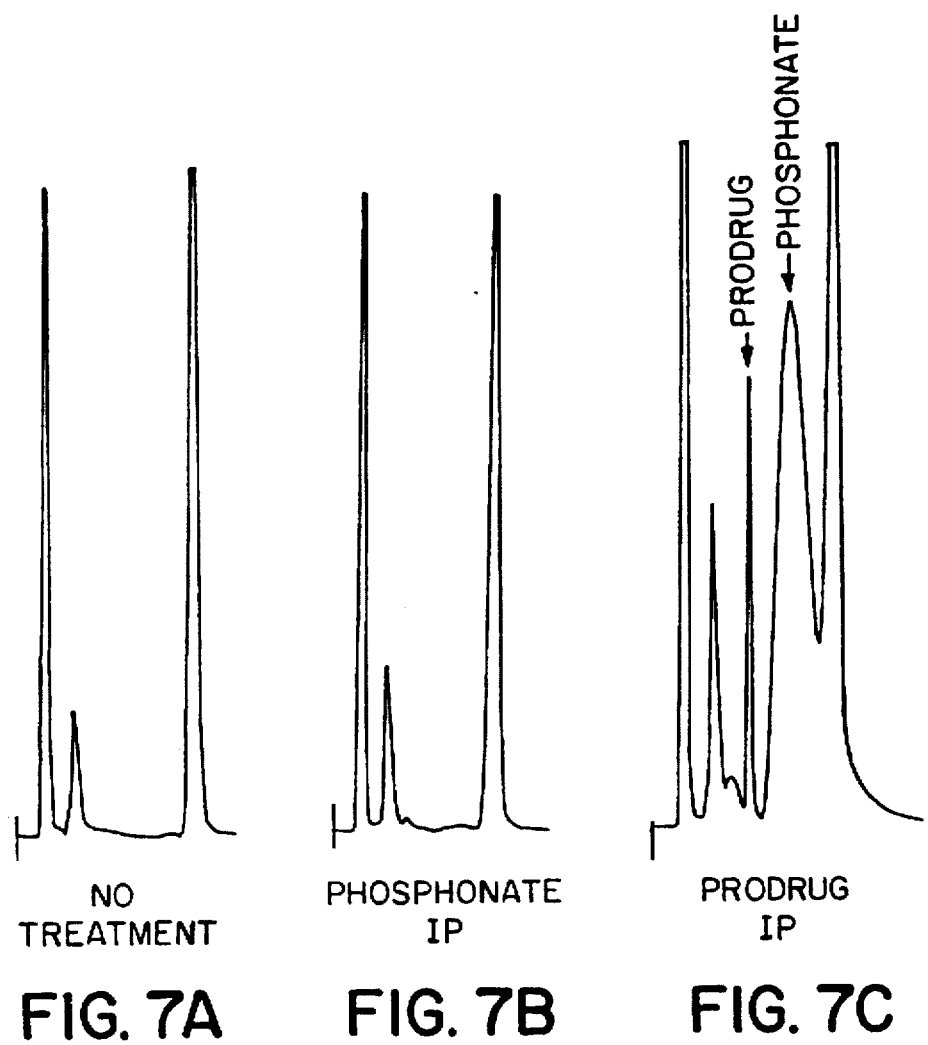

NO TREATMENT

PHOSPHONATE IP

PHOSPHONATE

PRODRUG IP

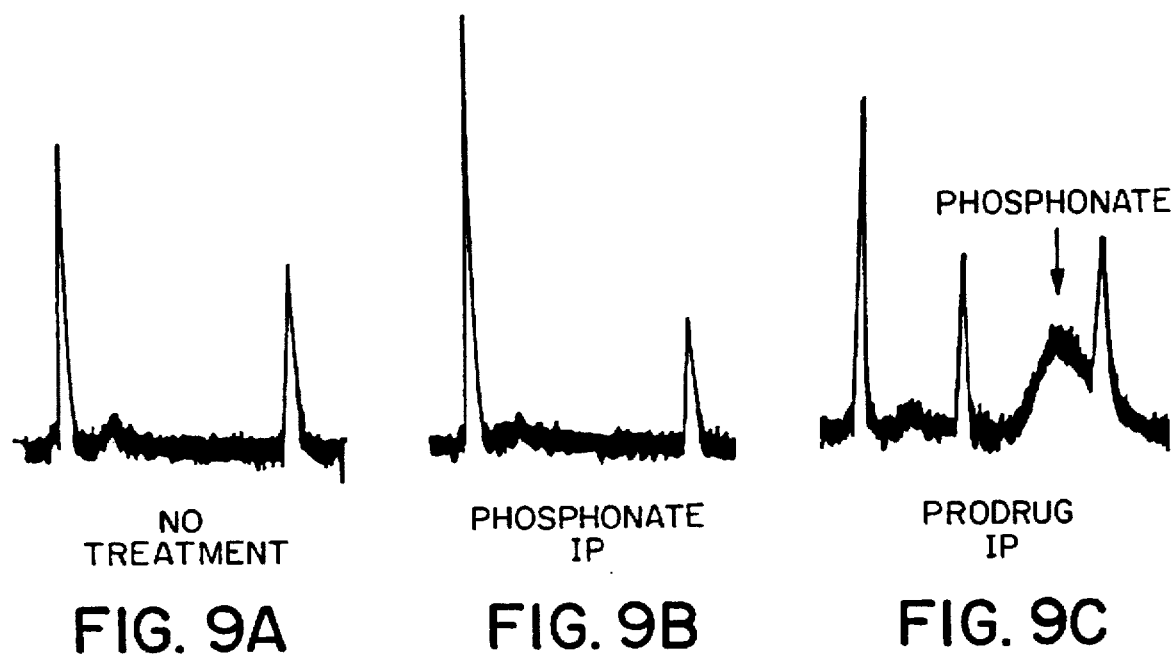

1

PHOSPHORUS PRODRUGS

RELATED APPLICATION

This application is a division of application Ser. No. 08/310,972 filed Sep. 23, 1994, now U.S. Pat. No. 5,627, 165, which is a Continuation-In-Part of U.S. Ser. No. 07/714,130 filed on Jun. 11, 1991, now abandoned, which is a Continuation-In-Part of U.S. Ser. No. 07/537,332 filed Jun. 13, 1990, now abandoned.

All of the above applications are incorporated herein by reference in their entirety.

TECHNICAL FIELD

This invention is in the fields of chemistry, medicine, and pharmacology.

BACKGROUND

Phosphate derivatives are key metabolic intermediates in virtually all aspects of cellular metabolism. In addition many antineoplastic and antiviral drugs require intracellular phosphorylation in order to be biologically active. However, the pharmacological utility of phosphate derivatives is severely hampered by the inability of negatively charged phosphate derivatives to permeate into cells and through the blood brain barrier.

Studies have been published describing lipophilic, negatively charged phosphate derivatives of Arabino-furanosylcytosine (ARA-C). E. K. Ryu et al., *J. Medicinal Chem.*, 25:1322 (1982); C. I. Hong et al., *J. Medicinal Chem.*, 28:171 (1985); A. Rosowsky et al., *J. Medicinal Chem.*, 25:171 (1982). However, these prodrug derivatives form liposomal aggregates in water which lead to unacceptable pharmacological properties. MacCross et al., *Biochemical and Biophysical Research Comm.*, 116:368 (1983). Neutrally charged phosphorodiamidates have been suggested as phosphate prodrugs. M. E. Phelps et al., *J. Medicinal Chem.*, 23:1229 (1980). However, this method is ineffective. Chawla, R. R. et al., *J. Medicinal Chemistry*, 27:1733 (1984). Similarly, cyclic phosphoramidate derivatives have been tested as potential prodrugs without success. Kumar, A. et al., *J. Medicinal Chemistry*, 33:2368 (1990). Neutrally charged phosphate prodrugs with good leaving groups have been described. Chawla et al., ibid., Farrow, S. N. et al., *J. Medicinal Chemistry*, 33:1400 (1990). However, neutrally charged phosphate esters which have a good leaving group on the phosphorous are in general extremely toxic inhibitors of acetylcholinesterase. Holmstedt, B., *Pharmacological Reviews*, 11:567 (1959). Phosphotriester derivatives which lack acetylcholinesterase activity are in general not catabolized by cellular enzymes to phosphodiesters. Benzylic 3'5'cyclic monophosphate triesters have been employed as prodrugs for cyclic nucleotide monophosphate derivatives with variable success. Engels, J. et al., *J. Medicinal Chemistry*, 20:907 (1977); Beres, J. et al., *J. Medicinal Chemistry*, 29:494 (1986); Beres, J. et al., *J. Medicinal Chemistry*, 29:1243 (1986). Primary benzylic phosphate esters are alkylating agents and potentially toxic. In addition the slow rate of hydrolysis of benzyl phosphate diesters to phosphate monoesters precludes the use of dibenzyl phosphotriesters as prodrugs. Acyloxymethyl phosphate esters have been described as potential prodrugs. Farquhar, D. et al., *J. Pharmaceutical Sciences*, 72:325 (1983); Farquhar, D. et al., *Biorganic Chemistry*, 12:118 (1984). Acyloxyalkyl bis phosphonate esters have been tested as prodrugs for a phosphonate compound and were found to be ineffective. Iyer, R. et al., *Tetrahedron Let.*, 30:7141 (1989). Bis (pivaloyloxy-methyl) prodrugs of PMEA enhance intracellular PMEA delivery in vitro and have enhanced antiviral activity in vitro. However, the utility of these compounds is limited by chemical instability. Srinivas, R. V. et al., *Antimicrob Agents Chemother.*, 37:2247 (1993); Starrett, J. E. et al., *Antiviral Res*, 19:267 (1993); Starrett, J. E. et al., *J. Med.Chem.*, 37:1857 (1994). The bis (pivaloyloxymethyl) prodrug of PMEA is undetectable in the blood of animals following oral administration. Only PMEA is detectable. The bis (pivaloyloxymethyl) prodrug of PMEA increases the oral absorption of PMEA to about 27% by acting at the level of the gastrointestinal tract. However, it does not enhance the delivery of PMEA at the tissue level. Cundy, K. C. et al., *Pharmaceutical Res.*, 11:839 (1994). Acyloxyalkyl prodrugs of PMEA also do not display significantly enhanced activity against the AIDS virus. Starrett, J. E. et al., *Antiviral Research*, 19:267 (1992). Bis phosphoesters of 2,2'dithioethanol are highly effective prodrugs in vitro. Puech, F. et al., *Antiviral Research*, 22:155 (1993). However, the metabolism of these prodrugs generates 2 mole equivalents of ethylene sulfide, which is extremely toxic. Lactyl, glycolyl, and alaninyl phosphates have also been tried as prodrugs with variable success. McGuigan, C. et al., *Antiviral Research*, 17:197 (1992).

SUMMARY OF THE INVENTION

The present invention relates to prodrugs which will allow the intracellular delivery of a wide range of phosphate and phosphorous bearing drugs, and methods for making the prodrugs. The method of the invention yields lipophilic, neutrally charged prodrugs which lack anticholinesterase activity.

In the present process, the parent phosphorous bearing drug is converted into a prodrug by coupling a unique class of substituted benzyl derivatives to one or more hydroxy group(s) on the phosphorous. A key feature of this class of prodrug is the presence of a masked hydroxy group in a para and or ortho position relative to the phosphoester Unmasking of this hydroxy group triggers heterolytic fission of the phosphoester. In some embodiments of this invention the unmasking of a hydroxy group triggers an elimination reaction with the release of the phosphorus bearing drug and the formation of a carbon-carbon double bond. This invention also relates to the methods of preparing and of administering the prodrugs.

BRIEF DESCRIPTION OF THE DRAWINGS

FIG. 7 is an illustration of high pressure liquid chromatograms of mouse liver samples employing fluorescent detection. Shown are results from a normal mouse, a mouse treated with the dansyl phosphonate (Structure 8), and a mouse treated with the dansyl phosphonate prodrug (Structure 9). Dramatically increased levels of the dansyl phosphonate are present in the prodrug treated liver.

FIG. 9 is an illustration of high pressure liquid chromatograms of mouse spleen samples employing fluorescent detection. Shown are results from a normal mouse, a mouse treated with the dansyl phosphonate (Structure 8), and a mouse treated with the dansyl phosphonate prodrug (Structure 9). The dansyl phosphonate is detectable only in the spleen of the prodrug treated mouse.

DETAILED DESCRIPTION OF THE INVENTION

Figure 1:
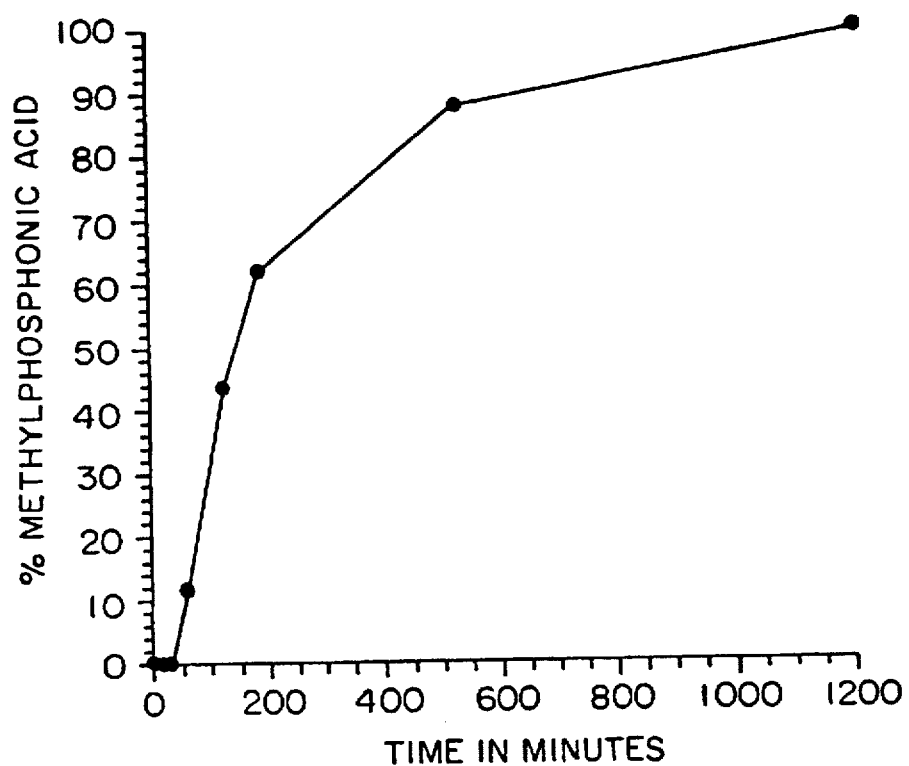
FIG. 1 is a graphic illustration of the kinetics of methylphosphonic acid production from Bis ((3-(ethyl 3-hydroxy-3-(4-acetoxyphenyl)propionate)) methylphosphonate upon treatment with pig liver esterase.

The present invention is a widely applicable, pharmacologically viable, method for making prodrugs and the products of this process which will allow the delivery of phosphorous bearing drugs into cells and through the blood brain barrier. The term "prodrug" is meant for the present purposes to encompass the class of drugs the pharmacologic action of which results from conversion by metabolic processes within the body (i.e., biotransformation).

In the present process, the parent phosphorous bearing drug is transformed into a prodrug by converting one or more of the hydroxy groups on the phosphorous into a phospho-ester, e.g. phosphate. The special nature of the class of phospho-esters employed in the prodrug design is central to the process. The phospho-ester is designed to undergo in vivo degradation via heterolytic cleavage of the C—O bond of the ester group.

The methods described herein for producing prodrugs allow for the facile intracellular delivery of an enormous range of phosphorous derivatives. This is of special importance since phosphate derivatives are key metabolic intermediates of virtually all aspects of cellular metabolism. Analogs of naturally occurring phosphate compounds can be useful as both research tools and as drugs. The ability to deliver these phosphate analogs into cells in a pharmacologically viable manner will be an advance in medicinal chemistry.

The protective groups of the invention can also be used in chemical synthesis as a protective group for phosphate or phosphonates. In organic synthesis there is often the need to temporarily protect a phosphate or phosphonate moiety as a diester or monoester. The present protective groups are readily removed by purified pig liver esterase under very mild conditions.

Phosphorous derivatives for which the present prodrug methods are potentially applicable include but are not limited to: monophosphate esters, phosphate diesters, phosphonates, phosphonate esters, phosphorothioates, thiophosphate esters, phosphonic acids, phosphinic acids, and phosphoramidates. In general any phosphorous containing drug which bears one or more hydroxy groups on the phosphorous atom(s) can be converted into lipid soluble prodrugs with the present process.

Drugs which can be converted into prodrugs according to the invention include those of, the following Structure 1:

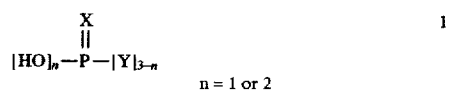

n = 1 or 2 wherein X can be oxygen (O) or sulphur (S) and n=1 or 2. The structure(s) of group or groups Y (which can vary independently) together with the $PX(OH)_n$ is a phosphorus bearing parent drug.

Preferably, the prodrug is substituted by a benzyloxy group which is α-substituted by a moiety which upon cleavage of the phosphoester will undergo in vivo an elimination reaction to form a carbon-carbon double bond at the α-carbon. Alternatively or additionally, a preferred prodrug of the invention is degraded to the parent phosphorous bearing drug by an elimination reaction triggered by the spontaneous or enzymatic unmasking of a strongly electron donating group, such as a hydroxy or amino group at the ortho or para positions of a benzyloxy group.

Since the prodrug derivatives are lipid soluble they will exhibit enhanced penetration through the blood brain barrier. The relationship between lipid solubility and enhanced drug absorption into the brain is well established. Dearden, J., Comprehensive Medicinal Chemistry, 4:402, Editors Hansch. C. et al., Pergman Press, New York, N.Y. Lipid solubility, according, is a desirable property for drugs, such as antineoplastic and antiviral drugs.

The prodrugs of the invention are synthesized by replacing one or more of the hydroxy groups on the phosphorous atoms of the parent drug with a group "A", wherein the group "A" is a benzyl-oxy- derivative with one or more acyl-oxy- groups in ortho or para positions relative to the phosphoester; and wherein the parent drug is liberated following conversion of the acyl-oxy- groups corresponding into the hydroxy group.

Preferably, the prodrugs of the invention are synthesized by replacing one or more of the hydroxy groups on the phosphorous atoms of the parent drug with a group "A" of the following structure 2:

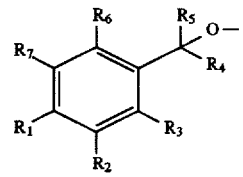

Wherein R1, R3, and R6 are independently an acyloxy group such as (—O—CO—R8); a carbonic acid ester group such as (—O—CO$_2$—R8); an N-substituted aminocarbonyloxy group such as (—O—C(O)—NHCH$_3$) or (—O—C(O)—N(CH$_3$)$_2$); a hydrogen; a halogen; a (—CO$_2$R9) group; an alkyl group such as methyl; a hydroxymethyl group (HO—CH$_2$—); a hydroxyethyl group or a —CH$_2$CO$_2$R$_{11}$ group or an inert group such as trifluoromethyl.

R2 and R7 are independently, hydrogen; or an inert group such as a carboxylic acid ester group such as (—CO$_2$R10); an alkyl group such as a methyl group; a halogen; an alkoxy group such as a methoxy group; an acyloxy group such as (—O—CO—R8); or a hydroxymethyl group (HO—CH$_2$—).

R4 and R5 are independently hydrogen; an alkyl group such as methyl, an alkoxyalkyl group such as methoxymethyl (—CH$_2$—O—CH$_3$); a carboxylic acid ester substituted alkyl group such as (—CH$_2$—CO$_2$—R12) or (—CH(CH$_3$)—CO$_2$—R12); an acyl alkyl group such as (—CH$_2$—CO—CH$_3$); an aminocarbonylalkyl group such as (CH$_2$—CONH$_2$) (—CH$_2$—CO—NHCH$_3$) or (—CH$_2$—CO—N ($CH_3$)$_2$); a nitro alkyl group such as (—$CH_2$—$NO_2$); or an alkylsulfonylalkyl group such as (—$CH_2$—$SO_2$—$CH_3$) or another group which will undergo an elimination reaction in vivo.

Wherein R8 is an alkyl group such as (—($CH_2$)$_N$—$CH_3$) (N can be from 0 to about 30, particular 0–18), isopropyl or t-butyl; a substituted or unsubstituted phenyl group, or a group such that (H—O—CO—R8) is an amino acid, lactic acid, glycolic acid, acetoacetic acid or a group such the resulting ester moiety is degraded to the free phenolic hydroxy group in vivo.

Wherein R9, R10, R11, and R12 are independently alkyl groups such as methyl or ethyl; or substituted or unsubstituted phenyl or benzyl groups;

With the proviso that at least one of the following groups: R1; R3; R6 is an acyloxy group, such as (—O—CO—R8); a carbonic acid ester group such as (—O—$CO_2$—R8); an N-substituted aminocarbonyloxy group, such as (—O—C(O)—$NHCH_3$) or (—O—C(O)—N($CH_3$)$_2$); or another group which undergoes biotransformation or spontaneous transformation in vivo to ultimately yield a hydroxy group on the phenyl ring in an ortho or para position.

The nature of the labile groups at R1, R3, and R6 determines the rate at which the resulting prodrug is transformed to the parent phosphorus bearing drug. The solubility of the prodrug can be varied by changing the nature of the groups R1–R8. Water solubility can be enhanced by selecting substituents with hydrophilic groups. Alternatively, one can select bulky substituents which disrupt intermolecular forces in the solid phase and lower the prodrug's melting point. Anderson, B., *Physical Chemical Properties of Drugs*, Edited by Yalkoswsky, S., pages 231–266; Marcel Dekker Inc., New York.

In the above description the term "inert" is used to refer to groups that are nonreactive and to not influence in a major fashion the chemistry of the prodrug metabolism or decay.

For parent drugs of Structure 1, the resulting prodrug has the Structure 3 shown below:

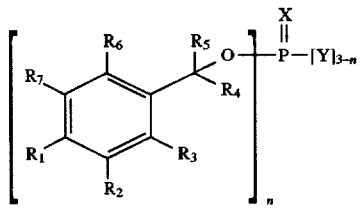

3

If the parent drug has the structure wherein n=1, the drug has the formula (wherein the groups Y can vary independently) shown below:

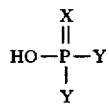

Then the prodrug has the formula:

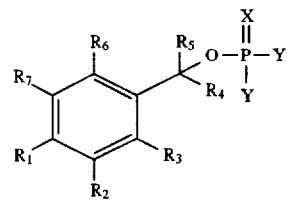

If the parent drug has the structure wherein n=2, the drug has the structure:

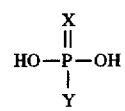

Then the prodrug has the formula:

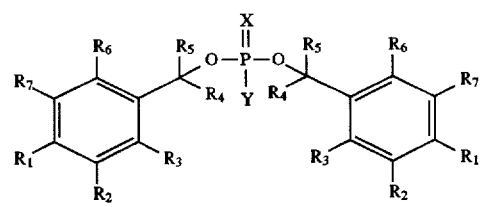

Wherein R1–R7 and X, and Y are as defined previously for Structures 1 and 2.

PREFERRED EMBODIMENTS OF THE PRODRUG METHOD

Some preferred embodiments of the prodrug method consist of replacing one or more of the hydroxy groups on the phosphorous with a group of the structures shown below as Structures 4A–4D:

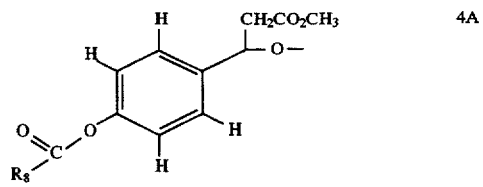

4A

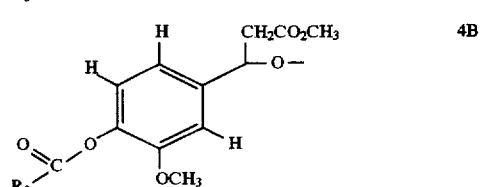

4B

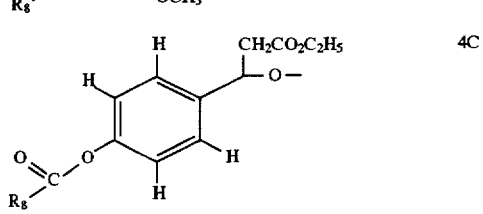

4C

-continued

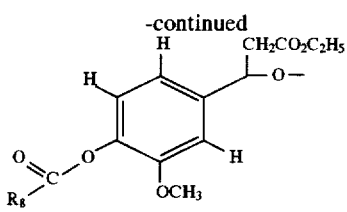

4D

Wherein R8 can in general be any group such that the resulting acyloxy moiety is degraded to the free hydroxy group intracellularly. Some preferred embodiments for the group R8 are the following: methyl; ethyl; phenyl; isopropyl; t-butyl; and the selection of R8 such that the structure R8—$CO_2H$ is an amino acid. For example R8 can be an aminomethyl group $NH_2$—$CH_2$— in which case R8—$CO_2H$ would be the amino acid glycine.

A key feature of this class of prodrug is the presence of a masked hydroxy group in a para and or ortho position relative to the phosphoester. Unmasking of this hydroxy group triggers heterolytic fission of the phosphoester.

The following basic chemical principles were exploited in the design of these prodrugs:

1) Benzyl derivatives undergo solvolysis at rates that are well described by the Hammet equation. Okamoto, Y. and Brown, H. C., *J. Org. Chem.*, 22:485 (1956). For example, the value of the reaction constant depends upon the substituents on the carbon atom to which the phenyl analog is attached. The reaction constant for the solvolysis of t-cumyl derivatives is −4.5. A minimum estimate of the absolute value of the reaction constant for the SN1 solvolysis of the prodrugs is 4.5. Prodrugs in which the substituents R4 and R5 are less electron donating then the methyl group will have a larger+charge in the transition state and a more negative value or the reaction constant. Lowry, T. H. and Richardson, K. S., *Mechanism and Theory in Organic Chemistry*, 2nd ed. Harper and Row Publishers, New York, N.Y. page 354–356 (1981).

2) Acyloxy groups are only very slightly electron donating. For example the Hammett para sigma+constant for the acetoxy group is −0.06. In contrast the hydroxy group is strongly electron donating. The Hammett sigma para+ constant for the hydroxy group is −0.92. The ionized hydroxy group (—O—) is even more electron donating with a Hammett para sigma+constant that has been estimated at −2.3. Chapman, N. B. and Shorter, J., *Correlation Analysis in Chemistry*, Plenum Press, New York, N.Y., page 483–484; Vogel, P., *Carbocation Chemistry*, Elsevier, New York, N.Y. (1985) page 243; Hansch, C., *Comprehensive Medicinal Chemistry*, Pergamon Press, New York, N.Y., 4:235.

3) Nonspecific esterase is ubiquitous within the cytoplasm of cells and is able to cleave a wide variety of carboxylate esters. Cleavage of the acyloxy group(s) of the prodrug will trigger heterolytic fission of the C—O bond of the phosphoester. Based on the above considerations the conversion of the group R1 into a hydroxy group will lead to a rate increase of phosphoester fission of at least 7000 fold. The compound in which R1 is ionized to an oxyanion, O—, will undergo solvolysis at a rate of about $2\times10^{10}$ fold greater. Based on an intracellular pH of 7 and a pKa of 10 for the phenolic hydroxy group about 0.1% of the hydroxy groups will be ionized under physiological conditions. The net result is that overall a rate increase on the order of $2\times10^7$ fold will occur in the solvolysis reaction following cleavage of a para acyloxy group by nonspecific esterase. Similar rate enhancements are expected if the acyloxy group is in the ortho position.

Without being limited to a particular reaction the mechanism by which the prodrugs undergo transformation to the parent drug is shown below in Scheme 1:

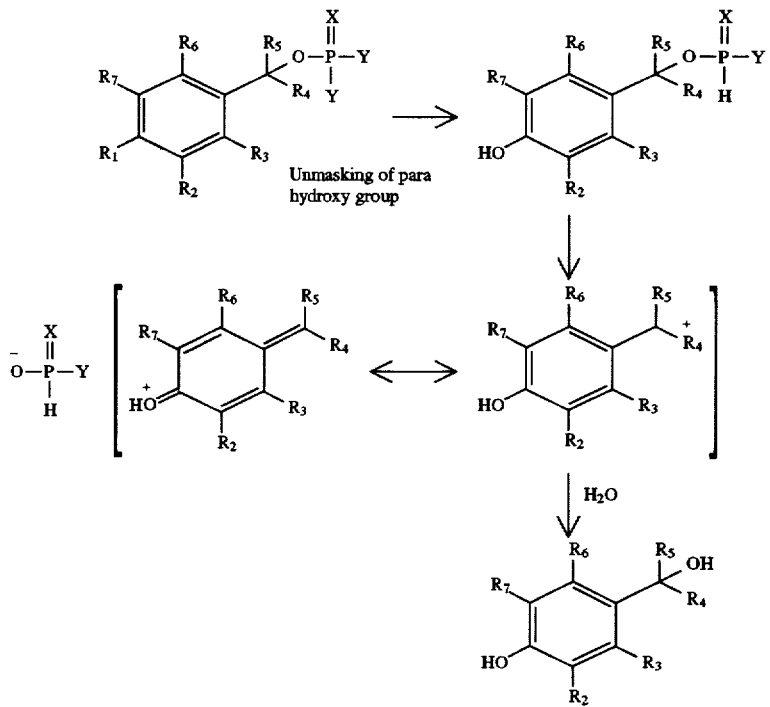

In this schematic R1–R8, X, and Y are as described for Structures 1 and 2. The carbocation shown above can also decay by an elimination reaction which is not shown in the above figure.

4) The rate of spontaneous hydrolysis of the prodrug is a function of the sum of the Hammet sigma+constants of the substituents on the benzyl ring and a function of the Hammet sigma+constants of the groups R4 and R5.

TOXICOLOGICAL CONSIDERATIONS

Neutrally charged phosphorous derivatives are among the most toxic compound known. The toxicity is due to the ability of the compounds to cause suicide inhibition of the enzyme acetylcholinesterase. The present prodrugs were specifically designed to avoid this toxicity. The ability of phosphate esters and related compounds to inhibit acetylcholinesterase is a sensitive inverse function of the pKa of the esterified alcohol group. Ashani, Y. et al., *J. Medicinal Chem.*, 16:446 (1973). The high pKa of the esterified alcohol group in the present prodrug method effectively precludes anticholinesterase activity.

The carbocation that results from the heterolytic cleavage of the C—O bond during the transformation of the prodrug to the parent drug will be consumed by reaction with water to form an alcohol, by an elimination reaction, or by an intramolecular nucleophilic reaction. The exact mechanism (s) of carbocation decay will depend upon the nature of the substituents on the carbocation.

ILLUSTRATIONS OF THE CHEMISTRY OF THE PRODRUG METHOD

To demonstrate the mechanism of action of the prodrug method methylphosphonic acid was employed as a model compound. Neutrally charged lipophilic derivatives of methylphosphonic acid were prepared using two representative embodiments of the prodrug methodology. The transformation of these compounds to methylphosphonic acid via nonspecific esterase was then demonstrated.

Bis (4-acetoxy-3-methoxybenzyl) methylphosphonate

Synthesis: 4-acetoxy-3-methoxybenzyl alcohol

A solution of 4-acetoxy-3-methoxybenzaldehyde (Aldrich) 10 grams (0.05 Moles) in 200 ml of ethanol was treated with 10% palladium on carbon (1.0 gram) and hydrogenated on a Parr apparatus at a pressure of 20 PSI until no further uptake of hydrogen was observed. The catalyst was removed from the mixture by filtration with celite and washed with 50 ml of ethanol. The combined filtrates were concentrated with an aspirator at 40° C. to give an oil. The oil was dissolved in 100 ml of toluene, concentrated at 40° C. with an aspirator and dried at 0.01 mm Hg at room temperature to give 10 grams (ca. 100% yield) of product as a colorless oil. Proton NMR in $CDCl_3$, at 60 MHZ with TMS as standard revealed: at 2.27 (3H, singlet); at 3.76 (3H,singlet); at 4.53 (2H, singlet) 6.9–7.3 (3H, multiplet).

Bis (4-acetoxy-3-methoxybenzyl) methylphosphonate

A solution of 4-acetoxy-3-methoxy-benzyl alcohol (2.94 gms, 15 mmol) in 20 ml of anhydrous diethyl ether containing n-methylimidazole (0.82 gms, 10 mmol) (Aldrich) and triethylamine (1.01 gms, 10 mmol) under a nitrogen atmosphere was treated with 0.66 gms (5 mmol) of methylphosphonic dichloride (Aldrich). The mixture was stirred for 10 minutes at room temperature, diluted with 100 ml of methylene chloride and cooled to 5° C. Water 50 ml was added dropwise over a period of 20 minutes to the mixture which was kept at a temperature of 5°–10° C. The organic phase was separated, washed times 2 with 25 ml of 5% aqueous sodium bicarbonate, water (25 ml×2), and 25 ml of saturated aqueous sodium chloride. The organic phase was dried with $MgSO_4$ and concentrated with an aspirator at 25° C. followed by drying at 0.01 mm Hg at room temperature overnight to give approximately 2.5 gms of product as a colorless oil.

Proton NMR in $CDCl_3$ at 60 MHZ with TMS as standard revealed: at 1.5 (3H doublet, J 18 Hz); 2.30 (6H, singlet); at 3.83 (6H singlet); at 5.0 (4H, doublet, J 10 Hz); 6.8–7.3 (6H, multiplet).

For some studies the above preparation of bis (4-acetoxy-3-methoxybenzyl) methylphosphonate was subjected to further purification by additional partitioning between chloroform and aqueous sodium bicarbonate. The organic phase was then dried and removed exvacuo.

Degradation Studies

The conversion of the model prodrug compound; bis (4-acetoxy-3-methoxybenzyl) methylphosphonate was examined using a Varian Unity 300 MHZ NMR Spectrometer. Porcine liver esterase was purchased from Sigma Chemicals. The porcine liver esterase had an activity of 230 units/mg. The kinetics of decomposition of the model compound was followed by taking serial NMR spectra. The experiments were conducted with 8 mg of the model compound in 0.75 ml of deuterium oxide buffered to pH 7.2 with Tris(hydroxy-d-methyl)amino-$d_2$-methane at 37° C. In early experiments the Tris buffer was 0.05M. In later experiments the Tris molarity was increased to 0.10M which provided for better pH control. Bis (4-acetoxy-3-methoxybenzyl) methylphosphonate ester, mono (4-acetoxy-3-methoxybenzyl) methylphosphonate ester, and methyl-phosphonic acid were readily distinguished by the differing chemical shifts of the methyl protons which were coupled to the phosphorous.

In the absence of esterase Bis (4-acetoxy-3-methoxybenzyl) methylphosphonate was relatively stable. The compound was observed to undergo slow solvolysis to mono (4-acetoxy-3-methoxybenzyl) methylphosphonate and 4-acetoxy-3-methoxybenzyl alcohol. This occurred with a half life of approximately 10 hours.

In the presence of porcine liver esterase (40 micrograms) Bis (4-acetoxy-3-methoxybenzyl) methylphosphonate was degraded to acetic acid, 4-hydroxy-3-methoxybenzyl alcohol and mono (4-acetoxy-3-methoxybenzyl) methylphosphonate. This reaction occurred extremely rapidly with a half life much less then 1 minute. At 1 minute the bis ester was no longer detectable. The mono (4-acetoxy-3-methoxybenzyl) methylphosphonate was in turn degraded to methylphoshonic acid, acetic acid, and 4-hydroxy-3-methoxybenzyl alcohol. This reaction occurred with a half life of approximately 16 minutes. After 90 minutes monoester was no longer detectable. To verify that the observed degradation product was indeed methylphosphonic acid a small quantity of authentic methylphosphonic acid was added to the NMR tube. As expected the NMR absorption peaks were identical.

The reaction pathway is illustrated below:

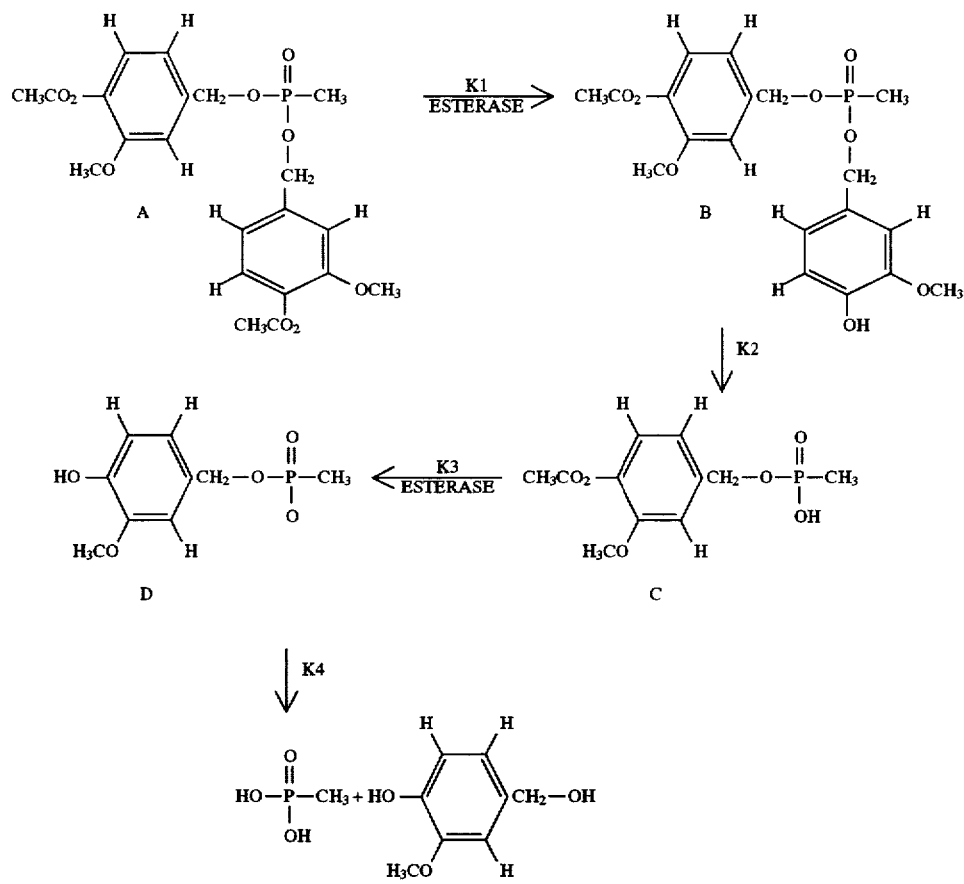

The rate constants K2 and K4 are likely very large since structures B and D are not detectable in the NMR spectra.

The second illustration of the chemistry of the prodrug method again employs methylphosphonic acid as a model phosphonate compound. The bis ester of ethyl 3-hydroxy-3-(4-acetoxyphenyl)propionate was synthesized. Treatment with nonspecific esterase resulted in the transformation of this compound to methylphosphonic acid and 4-hydroxycinnamic acid and ethyl 4-hydroxycinnamate.

Synthesis: ethyl 3-hydroxy-3-(4-acetoxyphenyl) propionate

This novel compound was synthesized by the acylation of 4-hydroxyacetophenone with diethylcarbonate to yield ethyl 4-hydroxybenzoylacetate. Treatment with acetic anhydride and subsequent catalytic hydrogenation yielded the desired product. The experimental details are given below:

Synthesis of ethyl 4-hydroxybenzoylacetate 50 ml of diethylcarbonate (Aldrich Chemicals) was heated to refluxed at 126° C. under nitrogen with a Vigreaux column leading to a short path distillation apparatus. Then the oil bath was removed and 3.0 grams of sodium was slowly added. A thick purple-brown slurry formed. The mixture was then heated to 140° C. and a solution of 6.0 grams of 4-hydroxy-acetophenone, (Aldrich) in 60 ml of diethylcarbonate was slowly added. The reaction mixture became lighter in color and more viscous. Ethanol began to distill and 11 ml were collected. The oil bath temperature was increased to 180° C. and the mixture was heated until the distillate temperature exceeded 120° C. The mixture was then cooled to 30° C. and poured onto 30 ml of 3N HCl and 30 ml of crushed ice. The flask was then rinsed with another 10 ml of 3N HCl and 10 ml of crushed ice. The yellow organic layer was separated and the aqueous phase was extracted twice with 50 ml of ether. The combined organic phases were then dried over magnesium sulfate. The organic extracts were then filtered and dried to give 8.2 grams of a crude product as a yellow oil. The oil was then purified by flash chromatography on silica gel with 15% ethyl acetate/petroleum ether. 4.2 grams of the ethyl 4-hydroxybenzoylacetate were isolated.

Proton NMR in $CDCl_3$ at 60 MHZ with TMS as standard revealed: at 1.27 (3H triplet); 4.0 (2H, singlet); at 4.26 (2H quartet); at 6.9 (2H, doublet); at 7.9 (3H, doublet).

Synthesis of ethyl 4-acetoxy-benzoylacetate 1.85 grams of ethyl 4-hydroxybenzoylacetate was added to 15 ml of anhydrous pyridine. 0.91 grams of acetic anhydride was added along with a few crystals of dimethylaminopyridine (Aldrich). After 1 hour at room temperature the pyridine was removed exvacuo. The oily residue was stirred with 25 ml of water and 25 ml of ether. The aqueous phase was separated and extracted twice with 50 ml of ether. The combined ether extracts were washed with 0.5N HCl (25 ml), then with saturated sodium bicarbonate solution (25 ml), and finally with 25 ml of brine. The extracts were then dried with magnesium sulfate, filtered and the ether removed exvacuo. To yield 2.07 grams of ethyl 4-acetoxybenzoylacetate.

Proton NMR in CDCl$_3$ at 60 MHZ with TMS as standard revealed: at 1.2 (3H triplet); at 2.27 (3H, singlet); at 4.0 (2H singlet); at 4.2 (2H quartet); at 7.2 (2H, doublet); at 8.0 (2H, doublet).

Synthesis: ethyl 3-hydroxy-3-(4-acetoxyphenyl) propionate
Method A

A 50 ml flask was flushed with nitrogen and charged with 1.0 grams of ethyl 4-acetoxy-benzoylacetate and 15 ml of methanol. Platinum dioxide (Aldrich, 0.05 gm) was added and the flask was flushed with nitrogen before being filled with hydrogen. The mixture was stirred at room temperature and atmospheric pressure. After 26.5 hours of reaction time an additional 25 mg of platinum dioxide was added. After 93 hours the reaction mixture was filtered through celite. The celite was washed with methanol. The combined filtrates were rotary evaporated to yield 0.95 grams of crude product as an oil. The oil was purified by flash chromatography on silica to give 0.33 grams of a yellow solid, which was recrystallized from 25% diethyl ether/petroleum ether. A total of 0.24 gm of white crystalline product identified as ethyl 3-hydroxy-3-(4-acetoxyphenyl) propionate was obtained. The melting point was 74°–75° C. Elemental analysis and NMR confirmed the product identity.

Proton NMR in CDCl$_3$ at 300 MHZ with TMS as standard revealed: at 1.265 (3H, triplet); at 2.203 (3H, singlet) at 2.715 (2H, doublet with second order splitting); at 3.332 (1H doublet); at 4.184 (2H, quartet); at 5.125 (1H, triplet with second order splitting); at 7.084 (2H, doublet); at 7.377 (2H, doublet).

Synthesis: ethyl 3-hydroxy-3-(4-acetoxyphenyl) propionate
Method B

A 250 ml round bottom flask was charged with 11.25 grams (0.045 mol.) of ethyl 4-acetoxy-benzoylacetate and 150 ml of diethyl ether. The solution was stirred and ammonia-borane (1.39 gm., 0.045 mol., Alfa) was added in 4 portions. After being stirred 90 minutes at room temperature 50 ml of ether were added and the reaction mixture was slowly poured into a 400 ml beaker containing 20 ml of 3N HCl and 100 ml of crushed ice. After 15 minutes the organic phase was separated. The aqueous phase was extracted with ether (2×100 ml). The combined organic phase was washed with brine, dried over magnesium sulfate, filtered and evaporated. The crude product was purified by flash chromatography, using a 7 cm. diameter column of 250 grams silica gel, packed and eluted with 25% ethyl acetate/ petroleum ether. 6.53 grams of ethyl 3-hydroxy-3-(4-acetoxyphenyl)propionate was obtained. The product was identical to that obtained by method A as determined by NMR and elemental analysis.

Synthesis: ethyl 3-hydroxy-3-(4-acetoxyphenyl) propionate
Method C

Ten grams of ethyl 4-acetoxy-benzoylacetate was dissolved in 100 ml of ethanol and 250 mg of 10% palladium on carbon (Aldrich) was added under argon. The mixture was then hydrogenated at room temperature on a Parr apparatus at a pressure of 40 pounds per square inch. When hydrogen uptake ceased, the mixture was filtered, and the solvent evaporated to yield the desired product in quantitative yield. Synthesis of: bis ((3-(ethyl 3-hydroxy-3-(4-acetoxyphenyl) propionate)) methylphosphonate One hundred mg of ethyl 3-hydroxy-3-(4-acetoxyphenyl) propionate was dissolved in 1.5 ml of dichloromethane (Anachemia, distilled over phosphorous pentoxide). N-Methylimidazole (Aldrich, 0.029 ml) and triethylamine (Aldrich, distilled over calcium hydride, 0.050 ml) were stirred into the solution. Methylphosphonic acid dichloride (Aldrich, 0.024 gm) in 0.50 ml of anhydrous dichloromethane was added to the stirred reaction mixture. The solution was stirred for 105 minutes at room temperature and then refluxed for 30 minutes.

The cooled solution was then diluted with 5 ml of dichloromethane and 3 ml of water was added. The organic layer was separated and washed successively with saturated sodium bicarbonate (2×5 ml), water (2×5 ml), and brine (5 ml). The organic phase was then dried over magnesium sulfate. The organic phase was then filtered and dried exvacuo to yield 0.107 grams of crude product. This product was then partially purified on a silica gel column which was eluted with 40% to 60% ethyl acetate in petroleum ether. The silica gel chromatography cleanly separated residual ethyl 3-hydroxy-3-(4-acetoxyphenyl)propionate from the products. The chromatography however, yielded incomplete separation of the mono and bis methylphosphonate esters from each other as evidenced by proton NMR and phosphorous NMR. The sample was further purified by hplc on a semiprep silica gel column (Rainin Dynamax Microsorb, 5 micrometer 1×25 cm) with chloroform:cyclohexane, 80:20, as eluent at a flow rate of 4.7 ml/min. Three fractions were isolated and examined by proton and phosphorous NMR. Fraction 1 was the d-l pair of the bis-ester, fraction 2 was the meso isomer of the bis isomer, fraction 3 was a mixture of the meso isomer of the bis ester and the mono-ester.

Analytical data for fraction 1 (d-l pair) is given below. Proton NMR in CDCl$_3$ at 300 MHZ with TMS as standard revealed: 0.11 (3H, doublet J=17.7 Hz); 1.207 (6H,triplet); 2.72 (2H, multiplet); 2.98 (2H, multiplet); 4.10 (4H, multiplet); 5.79(2H, quartet); 7.08(4H, doublet); 7.41 (4H, doublet). High resolution FAB mass spectroscopy revealed a molecular weight of 564.176 (+/−0.003). The calculated mass for $C_{27}H_{33}O_{11}P$ is 564.1743. This data confirmed that the isolated product was the desired bis ((3-(ethyl 3-hydroxy-3-(4-acetoxyphenyl)propionate)) methylphosphonate.

Degradation Studies

The degradation of Bis ((3-(ethyl 3-hydroxy-3-(4-acetoxyphenyl)propionate)) methylphosphonate was examined as described above in Example 1. Both the d-l pair and meso isomer were examined in separate experiments and behaved similarly. The compound was dissolved in D$_2$O containing 0.10M tris buffer at pH 7.2 and a temperature of 20° C.

In the absence of esterase the NMR spectrum remained unchanged over a time period of 1 hour. This indicates that both the mono and bis esters are stable under these conditions.

In the presence of porcine liver esterase (33 micrograms) the d-l pair was rapidly converted into acetic acid, mono ((3-(ethyl 3-hydroxy-3-(4-acetoxyphenyl)propionate)) methylphosphonate, and ethyl 4-hydroxycinnamate. By 30 minutes the bis ester was no longer detectable and 46% of the aromatic molecules present were ethyl 4-hydroxycinnamate. By 120 minutes hydrolysis of the acetoxy groups to acetic acid was essentially complete. An intermediate presumed to be mono ((3-(ethyl 3-hydroxy-3-(4-hydroxyphenyl)propionate)) methylphosphonate was noted by NMR. By 180 minutes 81% of the aromatic molecules were ethyl 4-hydroxycinnamate or 4-hydroxycinnamic acid. At 520 minutes 94% of the aromatic molecules were ethyl 4-hydroxycinnamate or 4-hydroxycinnamic acid. At 20 hours the NMR spectra revealed that the only products present were methylphosphonic acid, acetic acid, and trans 4-hydroxycinnamic acid, and ethanol.

To verify that the observed degradation product was indeed methylphosphonic acid a small quantity of authentic methylphosphonic acid was added to the NMR tube at 20 hours. As expected the NMR absorption peaks were identical.

The 4-hydroxycinnamic acid that was formed had the following NMR spectrum (300 MHZ) in the buffered D$_2$O: at 6.39 (1H doublet, J 15.9); 6.94 (2H doublet, J=8.7); 7.36 (1H, doublet J=16); 7.55(2H doublet J=9). A decoupling experiment demonstrated that the protons at shifts 6.4 and 7.4 were magnetically coupled. The kinetics of the liberation of methylphosphonic acid is shown in FIG. 1. The precise mechanistic details of the esterase catalyzed decomposition of Bis ((3-(ethyl 3-hydroxy-3-(4-acetoxyphenyl) propionate)) remains to be defined. However, it is clear that the compound is readily transformed by the action of nonspecific esterase into methylphosphonic acid and the elimination product 4-hydroxycinnamic acid. The overall reaction is summarized below:

phosphorous esters which undergo cleavage to the parent phosphorous acid by an elimination reaction which is triggered by the enzymatic unmasking of a hydroxy group in an ortho or para position on the phenyl ring. The powerful electron donating characteristics of the (ionized) hydroxy group promote heterolytic cleavage of the C—O bond of the phosphorous ester. An elimination reaction will result when the energy barrier for proton removal is significantly lower then the energy barrier for nucleophilic attack by solvent. The elimination reaction is favored by groups which lower the intrinsic barrier for proton removal. The transition state for proton removal is also likely stabilized by the partial formation of a conjugated double bond system. In the solvolysis of 1-phenylethyl chlorides only a small per cent of the carbocations decay via an elimination reaction to styrene. Richard, J. P. et al., *J. Am. Chem. Soc.*, 106:1373 (1984). In the model compound of Example 2 the function of the ethoxycarbonyl group is to increase the pKa of the protons on the adjacent carbon atom and to lower the intrinsic energy barrier for proton removal. This causes the carbocation that results from the solvolysis of the phosphonate to decay exclusively via an elimination reaction. It should be emphasized that other groups such as —CO—CH$_3$, —CO—NH$_2$, —NO$_2$, CH$_3$—SO$_2$—; which lower the intrinsic barrier for proton abstraction from an adjacent carbon atom can be employed in place of the ethoxycarbonyl

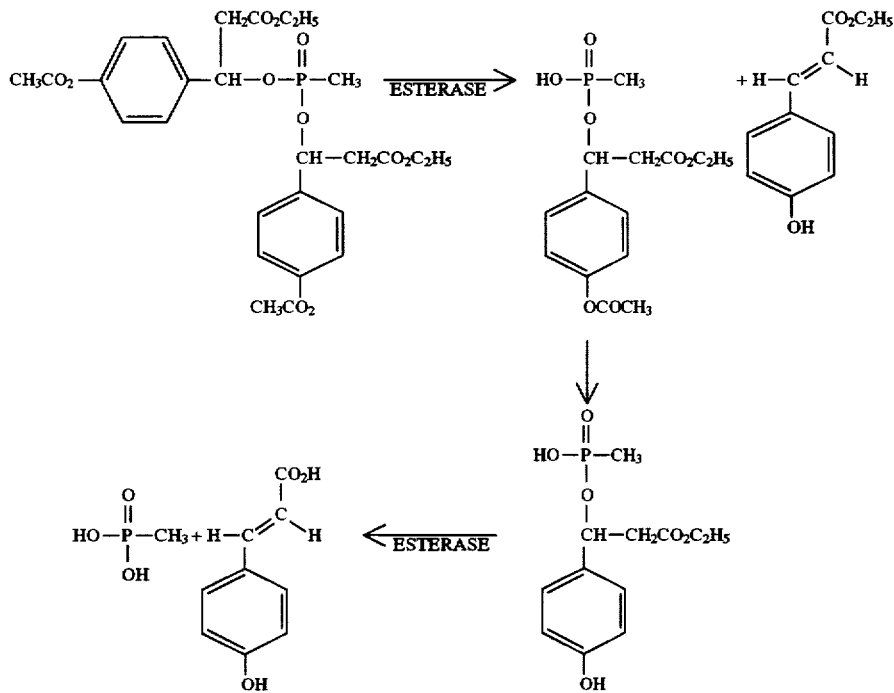

Regardless of the precise mechanistic details the results demonstrate that a compound such as methylphosphonic acid can be converted into a neutrally charged ester which is lipophilic using the present prodrug method. This is evidenced by solubility in organic solvents such as methylene chloride, chloroform, and diethyl ether. In the presence of nonspecific esterase the esters are rapidly transformed to the parent phosphonic acid. The function of the esterase is to unmask a hydroxy group which in turn leads to cleavage of the C—O bond of the phospho-ester. Bis ((3-(ethyl 3-hydroxy-3-(4-acetoxyphenyl)propionate)) methylphosphonate is a representative example of a new class of group and will similarly lead to carbocation decay via an elimination reaction. One skilled in the arts of chemistry will recognize other groups which also lower the intrinsic barrier for proton abstraction. These groups will work equally well to insure that the carbocation that results from the solvolysis of the prodrug will decay via an elimination reaction. These are to be considered within the scope of the present invention.

In the models discussed above a para hydroxy group is unmasked by the action of esterase. Similar electrical and resonance effects are expected for the stabilization of carbocation formation by a hydroxy or oxy anion group located in the ortho position. Fujita, T. et al., *Progress in Physical Organic Chemistry*; 12:49. Accordingly, a prodrug in which an ortho hydroxy group is unmasked via cellular enzymes will degrade in a similar manner.

In the models discussed above an ester group is cleaved by esterase to expose a hydroxy group on the phenyl ring. Phenolic carbonates and carbamates are also degraded by cellular enzymes to yield phenols. Dittert, L. et al., *J. Pharmaceutical Sci.*, 57:783 (1968); Dittert, L. et al., *J. Pharmaceutical Sci.*, 57:828 (1968); Dittert, L. et al., *J. Pharmaceutical Sci.*, 58:557 (1969); King, S. et al., *Biochemistry*, 26:2294 (1987); Lindberg, C. et al., *Drug Metabolism and Disposition*, 17:311 (1989); Tunek, A. et al., *Biochemical Pharmacology*, 37:3867 (1988). In addition a variety of carbonate and carbamate groups are known which undergo spontaneous cleavage in solution at kinetically favorable rates. Saari, W. et al., *J. Medicinal Chem.*, 33:97 (1990); Rattie, E. et al., *J. Pharmaceutical Sci.*, 59:1741 (1970).

A preferred element of the prodrug method is the presence of a group in an ortho or para position on the phenyl ring which is converted into a strongly electron donating group such as a hydroxy group or amino group. Since carbonates, and carbamates, and esters all are known to undergo this transformation in vivo any of these groups can be employed to mask the hydroxy group in the prodrug. Advantage can be made of the relative rate of metabolism of various masking groups to provide selective activation of the prodrugs in certain tissues. For example, carbamates are almost exclusively metabolized in the liver. Para-unsubstituted benzylic compounds also undergo para hydroxylation by hepatic enzymes. One skilled in the arts of medicinal chemistry will recognize other masking groups which enzymatically and/or spontaneously degrade to unmask a hydroxy group on phenyl ring. These groups can be employed in the present prodrug method and are to be considered to be within the scope of the present invention.

General Methods of Prodrug Synthesis Reagents

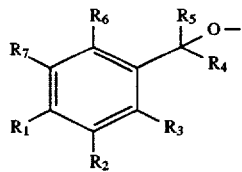

Formula 1

Prodrugs can be synthesized by a variety of chemical approaches from compounds of the structure shown as Formula 1.

Compounds given by the Formula 1 above are known compounds which can be purchased or readily synthesized by one skilled in the arts of organic chemistry using well known methodology. If R1–R6 has a hydroxy group or an amino group then it is necessary to protect this group prior to employing the phosphorylation methods given below. Suitable hydroxy protective groups include: trimethylsilyl-; tert-butyldimethylsilyl-; beta-(trimethylsilyl) ethoxymethyl; and vinyl ethers. These protective groups can be coupled to (and removed from) the hydroxy group of R1 and R6 using routine methods. Greene, T. W., *Protective Groups in organic Synthesis*, John Wiley and Sons, New York, N.Y. (1981).

Suitable protective groups for amino substituents on R1–R6 include the 9-Fluorenyl methoxycarbonyl group, the T-butoxycarbonyl (T-Boc) group and triazones. Carpino, L. *Accounts Chem. Res.*, 20:401 (1987); Knapp, S. et al., *Tetrahedron Lett.*, 31:2109 (1990).

For example, a suitable intermediate can be a compound of the structure:

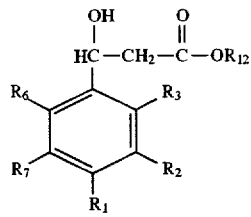

wherein $R_1$ is a (—$OCOR_{14}$) group; a (—O—CO—$R_{14}$) group; a (—O—CO—$NHCH_3$) group; or a (—O—CO—$N(CH_3)_2$) group;

wherein $R_2$ and $R_7$ are independently hydrogen, a (—$CO_2R_{10}$) group; a methyl group, a halogen, or a methoxy group, a (—O—CO—$R_8$) group, or a hydroxymethyl group (HO—$CH_2$); wherein $R_{10}$ may be a methyl or ethyl group;

wherein $R_3$ and $R_6$ are independently hydrogen; a methyl group; a hydroxymethyl group (—$CH_2$—OH); a halogen; or a hydroxyethyl group (—$CH_2$—$CH_2$—OH);

wherein $R_{14}$ is a alkyl group a substituted or unsubstituted phenyl group, or $R_{14}$ can be selected such that $R_{14}$—$CO_2H$ is; an amino acid; lactic acid; glycolic acid (—HO—$CH_2$—$CO_2H$); glyceric acid (HO—$CH_2$—CH(OH)—$CO_2H$); or acetoacetic acid ($CH_3COCH_2$—$CO_2H$)

An especially useful set of intermediates in prodrug synthesis is given by Formulae 1A below:

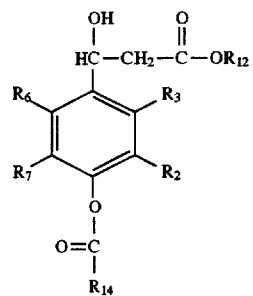

FORMULA 1A

Wherein R2, R3, R6, R7, and R12, are as described for Structure 2. Wherein R14 can be R8 or (R8—O—) where R8 is as defined in Structure 2. R14 can also be a group of the following such as: (—NHCH3); or (—N(CH3)2).

Compounds given by Formula 1A can be synthesized by reduction of the corresponding ketone given by Formula 1B shown below:

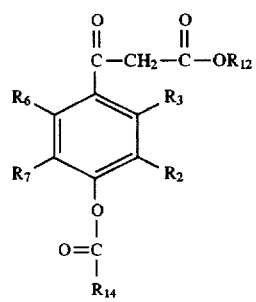

FORMULA 1B

Wherein R2, R3, R6, R7, R12, and R14 are as described for Formula 1A.

The alcohol given by Formula 1A can be synthesized from the keto compound given by Formula 1B by a variety of methods including: Catalytic hydrogenation with palladium on carbon, or platinum dioxide. Alternatively, the reduction can be effected by a reagent such as borane in ammonia.

Reduction of Formula 1B

Method A

A 50 ml flask is flushed with nitrogen and charged with 1.0 gram of Formula 1B in 15 ml of methanol. Platinum dioxide, 0.05 grams, is added and the flask is flushed with nitrogen before being filled with hydrogen. The mixture is stirred at room temperature and atmospheric pressure. After 24 hours of reaction time an additional 25 mg of platinum dioxide is added. After 90 hours the reaction mixture is filtered through celite. The celite is washed with methanol. The combined filtrates are rotary evaporated to yield crude product which is then purified by flash chromatography on silica. The reaction can also be run with the addition of a trace amount of a base such as pyridine to suppress reduction of the desired alcohol.

Method B

A 250 ml round bottom flask is charged with 0.045 moles of FORMULA 1B and 150 ml of diethyl ether. The solution is stirred and ammonia-borane (1.39 gm., 0.045 mol., Alfa) is added in 4 portions. After being stirred 90 minutes at room temperature 50 ml of ether are added and the reaction mixture is slowly poured into a 400 ml beaker containing 20 ml of 3N HCl and 100 ml of crushed ice. After 15 minutes the organic phase is separated. The aqueous phase is extracted with ether (2×100 ml). The combined organic phase is washed with brine, dried over magnesium sulfate, filtered and evaporated. The crude product is then purified by flash chromatography.

Method C

FORMULA 1B (0.05 moles) is dissolved in 100 ml of ethanol. After equilibrating with argon, 500 mg of 10% Pd on carbon (Aldrich) is added. The argon is then removed exvacuo and the mixture hydrogenated at 40 PSI at room temperature on a Parr hydrogenation apparatus. The progress of the reaction is monitored by TLC. After the reaction is completed the mixture is then filtered and the solvent removed exvacuo to yield the desired alcohol given by Formula 1A.

Synthesis of Formula 1B

Compounds given by Formula 1B can be synthesized by the following scheme:

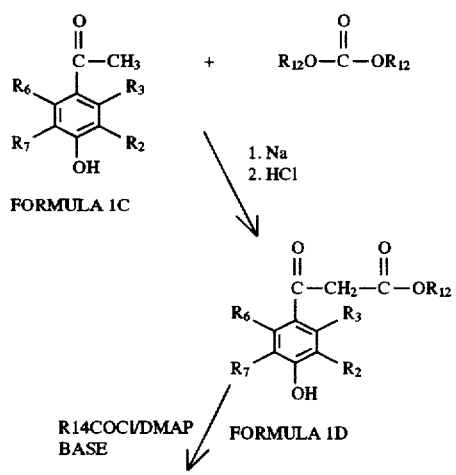

FORMULA 1B

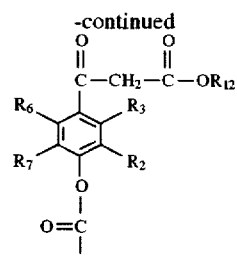

Synthesis of Formula 1B

Method A

Fifty ml of the carbonate (R12—O—CO—O—R12) is heated to refluxed under nitrogen with a Vigreaux column leading to a short path distillation apparatus. Then the oil bath is removed and 3.0 grams of sodium is slowly added. The mixture is then heated to 140° C. and a solution of 6.0 grams of the 4-hydroxy-acetophenone derivative (Formula 1C) in 60 ml of the carbonate is slowly added. The alcohol R12—OH is then removed by distillation. When the reaction has proceeded to completion the mixture is cooled to 30° C. and poured onto 30 ml of 3N HCl and 30 ml of crushed ice. The flask is then rinsed with another 10 ml of 3N HCl and 10 ml of crushed ice. The organic layer is separated and the aqueous phase is extracted twice with 50 ml of ether. The combined organic phases are then dried over magnesium sulfate. The organic extracts are then filtered and dried to give crude product which is then purified by flash chromatography on silica gel. The product is dissolved in pyridine and treated with 1 equivalent of the acid chloride (R14—CO—CL) or the related anhydride in the presence of a catalytic amount of dimethylaminopyridine (DMAP). After the reaction has proceeded to completion at room temperature the pyridine is removed exvacuo. The residue is stirred with 25 ml of water and 25 ml of ether. The aqueous phase is separated and extracted twice with 50 ml of ether. The combined ether extracts are washed with 0.5N HCl (25 ml), then with saturated sodium bicarbonate solution (25 ml), and finally with 25 ml of brine. The extracts are then dried with magnesium sulfate, filtered and the ether removed exvacuo.

General Methods of Prodrug Synthesis

Method A

In this method the compound given by Formula 1 is reacted with a chloride derivative of the parent phosphorous drug of the structure shown below as Formulae 3 and 4.

Formula 3

Formula 4

The reaction is carried out in a suitably inert anhydrous solvent such as pyridine, methylene chloride, ether, or tetrahydrofuran in the presence of a base such as triethylamine or pyridine. Catalysts such as: n-methylimidazole; 4-dimethylaminopyridine; 3-nitro-1,2,4-triazole; and 1-hydroxybenzotriazole can be employed.

Compounds given by Formulae 3 and 4 can be synthesized from the parent phosphorous bearing drug shown in Structure 1 by the following methods:

1) Treatment with thionyl chloride an in an inert solvent.
2) Treatment with trimethylchlorosilane in pyridine followed by the reaction of the resulting trimethylsilyl ester with thionyl chloride and a catalytic amount of dimethylformamide
3) Treatment with tris(2,4,6-tribromophenoxy)-dichlorophosphorane; Hotoda, H. et al., *Nucleic Acid Res.*, 17:5291 (1989); and
4) Treatment with refluxinqg 1,1, dichloromethyl ether.

The most expeditious route to the synthesis of compounds given by Formulae 3 and 4 depends upon the nature of the groups X and Y. For example, if X is oxygen, and Y is an alkoxy group then the compound given by Formula 4 can be readily synthesized by the action of phosphoryl chloride on Y—OH in the presence of a base. The key point is that compounds of the structure given by Formulae 3 and 4 can readily be synthesized by one experienced in the art of organic chemistry using known methods.

Method B

In this method a compound of the structure given by Formula 1 is reacted with a compound of the structure shown below as Formulae 5 and 6.

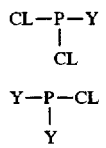

$$\begin{array}{c} CL-P-Y \\ | \\ CL \end{array} \quad \text{Formula 5}$$

$$\begin{array}{c} Y-P-CL \\ | \\ Y \end{array} \quad \text{Formula 6}$$

The reaction is carried out in a suitably inert anhydrous solvent such as pyridine, ether, or tetrahydrofuran in the presence of a base such as triethylamine or pyridine. Catalysts such as: n-methylimidazole; 4-dimethylaminopyridine; and 3-nitro-1,2,4-triazole can be employed. The product is then oxidized to yield the desired prodrug given by structure 3A or 3B. Suitable oxidants include: aqueous iodine; ethyl hypochlorite; and 3-chloroperoxybenzoic acid. Letsinger, R. L. et al., *J. Am. Chem. Soc.*, 98:3655 (1976).

Compounds given by Formulae 5 and 6 can be synthesized from the hydrogen phosphonate analog of the parent phosphorous bearing drug shown in Structure 1 by the action of tris(2,4,6-tribromophenoxy)-dichlorophosphorane. Hotoda, H. et al., *Nucleic Acid Res.*, 17:5291 (1989); Wada, T. et al., *Tetrahedron Lett.*, 29:4143 (1988).

If Y are alkoxy groups then the compound given by Formulae 4 and 5 can be synthesized by the action of phosphorous trichloride chloride on Y1—OH and Y2—OH in the presence of a base. The key point is that compounds of the structure given by Formulae 5 and 6 can readily be synthesized by one experienced in the art of organic chemistry using known methods.

Method C

In this method a compound of the structure given by Formula 1 is reacted with a compound of the structure shown below as Formulae 7 and 8.

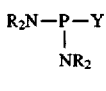

$$\begin{array}{c} R_2N-P-Y \\ | \\ NR_2 \end{array} \quad \text{Formula 7}$$

$$\begin{array}{c} Y-P-NR_2 \\ | \\ Y \end{array} \quad \text{Formula 8}$$

Wherein R is an alkyl group such as ethyl or isopropyl.

The reaction is carried out in a suitably inert anhydrous solvent such as ether, acetonitrile, or tetrahydrofuran in the presence of a catalyst such as 1-H-tetrazole or 1H,5-methyltetrazole. The product is then oxidized to yield the desired prodrug given by structure 3A or 3B. Suitable oxidants include aqueous iodine or ethyl hypochlorite.

Compounds of the structure given by Formulae 7 and 8 are readily obtained by the reaction of the desired dialkylamine with the chlorides derivatives given by Formulae 5 and 6. McBride, L. J. et al., *Tetrahedron Lett.*, 24:245 (1983); Perich, J. W. et al., *Tetrahedron Lett.*, 28:101 (1987); Hamamoto, S. et al., *Chem. Lett.*:1410 (1986); Marugg, J. E. et al., *Tetrahedron Lett.*, 27:2271 (1986); Letsinger, R. L. et al., *J. Am. Chem. Soc.*, 98:3655 (1976).

Method D

This method is similar to Method C above except that a compound of the structure shown below as Formula 9 is reacted with the parent drug (Y—OH). The resulting phosphite ester is then oxidized as described in Method C to the corresponding phosphate. The corresponding phosphorothioate can be readily made by treating the phosphite with a reagent such as 3H-1,2,Benzodithiol-3-one 1,1,-dioxide. Iyer, R. P., et al., *J. Organic Chem.*, 55:4693 (1990). Compounds given by Formula 9 below can be readily synthesized by the reaction of a compound given by Formula 1 with a dialkylphosphoramidous Dichloride in an inert solvent in the presence of a base such as triethylamine.

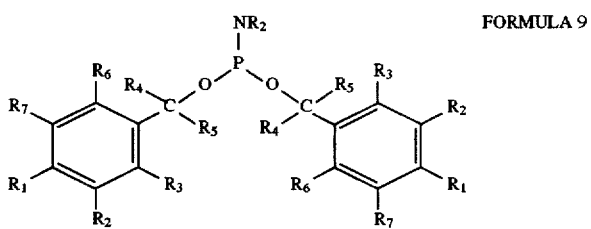

FORMULA 9

Wherein R is an alkyl group such as ethyl or isopropyl and R1–R8 are as described in Structure 2.

Nucleotide Monophosphate Prodrugs

A wide variety of biologically active nucleoside derivatives require phosphorylation in order to exhibit biological activity. For example, a major factor which determines inhibitory activity of a dideoxynucleoside analogs against the AIDS virus is the ability of the nucleoside to be phosphorylated. Zhang, H. et al., *Molecular Pharmacology*, 34:431 (1988); Balzarini, J. et al., *J. Biol. Chem.*, 264:6127 (1989). The ability of cells from differing tissues to phosphorylate a nucleosides is quite variable. The present prodrug method will allow the delivery of the monophosphate derivatives of a wide variety of antiviral nucleotides into cells and into the brain.

The present prodrug method can also be employed to deliver nucleotide analogs which possess antineoplastic activity into cells. For example, chain terminating nucleoside analogs can be selectively toxic for leukemic cells that possess the enzyme deoxyribonucleotidyl transferase (TDT). Spigelman, Z. et al., *Blood*, 71:1601 (1988). Cytotoxicity is likely dependent upon phosphorylation of the dideoxynucleoside into the corresponding triphosphate and incorporation of the chain terminating analog into the cellular DNA via TDT. The present prodrug method can be used to selectively kill TDT+leukemic cells that are deficient in nucleoside kinase activity.

General Structure of Nucleotide Monophosphate Prodrugs

The general structure for nucleotide monophosphate prodrugs is shown below as Formula 10

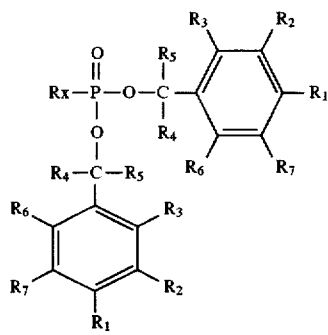

FORMULA 10

Wherein R1–R7 are as described for Structure 2 and Rx is the nucleosidyl group

General Methods for Synthesizing Nucleotide Monophosphate Prodrugs

In the following sections the term "protected nucleoside" refers to a nucleoside derivative in which potentially interfering groups are suitably protected. Routine methods of nucleoside protection and deprotection can be employed. Sonveaux, E., Bioorganic Chem., 14:274 (1986). The protecting groups are removed in the last step of prodrug synthesis.

Method A

Ten mMoles of phosphorous trichloride and 10 mMoles of triethylamine are added to 50 ml of anhydrous diethyl ether at –10° C. Then 10 mMoles of "protected nucleoside" in 30 ml of anhydrous ether is added to the rapidly stirred solution. After 4 hours an additional 20 mMoles of triethylamine and 35 mMoles of strictly anhydrous Formula 1 are added. After 6 hours the precipitated triethylamine hydrochloride is removed by filtration. Then 40 ml of water is slowly added. The organic phase is then separated and the solvent removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water. The protective groups are then removed using routine methods and the desired prodrug purified by crystallization from a suitable solvent or via chromatography on silica.

Method B

Ten mMoles of phosphorous trichloride and 10 mMoles of triethylamine are added to 50 ml of anhydrous diethyl ether at –10° C. Then 10 mMoles of "protected nucleoside" in 50 ml of anhydrous ether is added to the rapidly stirred solution. After 2 hours 40 mMoles of diisopropylamine is added and the mixture is warmed to room temperature for 3 hours. Then 30 mMoles of strictly anhydrous Formula 1 and 90 mMoles of 1-H-tetrazole are added. After 2 hours at room temperature the precipitated triethylamine hydrochloride and diisopropylamine hydrochloride are removed by filtration. Then the solvent is removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water. The protective groups are then removed using routine methods and the desired prodrug purified by crystallization from a suitable solvent or via chromatography on silica.

Method C

Ten mMoles of phosphorous oxychloride and 10 mMoles of triethylamine are added to 50 ml of anhydrous diethyl ether at –10° C. Then 10 mMoles of "protected nucleoside" in 50 ml of anhydrous ether is added to the rapidly stirred solution. After 4 hours an additional 20 mMoles of triethylamine, 20 mMoles of N-methylimidazole, and 20 mMoles of 1-hydroxybenzotriazole and 35 mMoles of strictly anhydrous Formula 1 are added. After 6 hours the precipitated triethylamine hydrochloride is removed by filtration. Then 200 ml of methylene chloride and 100 ml of water are added. The organic phase is separated, washed times 3 with 50 ml of 1M aqueous sodium bicarbonate followed by 50 ml×3 of water. The protective groups are then removed using routine methods and the desired prodrug purified by crystallization from a suitable solvent or via chromatography on silica.

Method D

Ten mMoles of phosphorous oxychloride and 10 mMoles of triethylamine are added to 50 ml of anhydrous diethyl ether at –10° C. Then 10 mMoles of "protected nucleoside" in 50 ml of anhydrous ether is added to the rapidly stirred solution. After 4 hours the precipitated triethylamine hydrochloride is removed by filtration. Then 20 mMoles of the lithium alkoxide derivative of Formula 1 in 50 ml of anhydrous diethyl ether is added at –78° C. under an inert atmosphere. After 6 hours the temperature is increased to room temperature for 2 hours. Then 100 ml of water is slowly added at 0° C. Then 200 ml of methylene chloride is added. The organic phase is then separated and washed times three with 100 ml of 1M aqueous ammonium chloride solution and washed times 4 with 100 ml of 1M aqueous sodium bicarbonate, followed by 100 ml×two of water, followed by 100 ml of saturated aqueous sodium chloride. The organic phase is dried with magnesium sulfate and the solvent is removed exvacuo. The desired prodrug can then be purified from the residue by flash chromatography on silica or by recrystallization from a suitable solvent.

Method E

Ten mMoles of phosphorous oxychloride and 30 mMoles of triethylamine and 30 mMoles of 3-nitro,1,2,4-triazole are added to 50 ml of anhydrous diethyl ether at room temperature. After 1 hour 10 mMoles of "protected nucleoside" in 20 ml of anhydrous ether is added to the rapidly stirred solution. After 4 hours 35 mMoles of strictly anhydrous Formula 1 are added. After 6 hours the precipitated triethylamine hydrochloride is removed by filtration. Then 200 ml of methylene chloride and 100 ml of water are added. The organic phase is separated, washed times 3 with 50 ml of 1M aqueous sodium bicarbonate followed by 50 ml×3 of water. The protective groups are then removed using routine methods and the desired prodrug purified by crystallization from a suitable solvent or via chromatography on silica.

Prodrugs for 3'azido-thymidine 5'monophosphate

The general structure of prodrugs for 3'azido-dideoxythymidine 5'monophosphate (AZT-phosphate) is shown below as Formula 11:

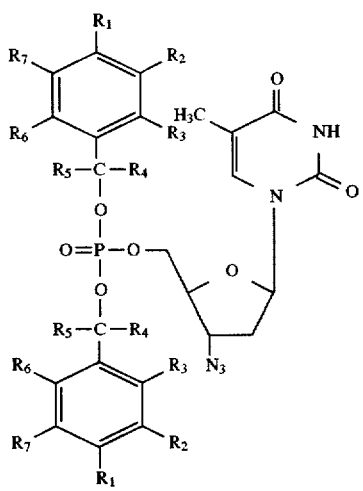

FORMULA 11

Wherein R1–R7 are as described for Structure 2

Prodrugs of Formula 11 can be employed to deliver AZT-phosphate into cells and into the brain. Although AZT has shown some promise in the treatment of HIV associated encephalitis the penetration of AZT into brain tissue is very poor. Terasaki, T. et al., *J. Inf. Dis.*, 158:630 (1988); Doshi, K. J. et al., *Drug Metab. Dispos.* 17:590 (1989).

The present prodrug will circumvent this problem. In addition the present prodrugs will prevent the multiplication of HIV in those tissues which do not adequately phosphorylate AZT.

An example of a prodrug for AZT-phosphate is shown below as Formula 12:

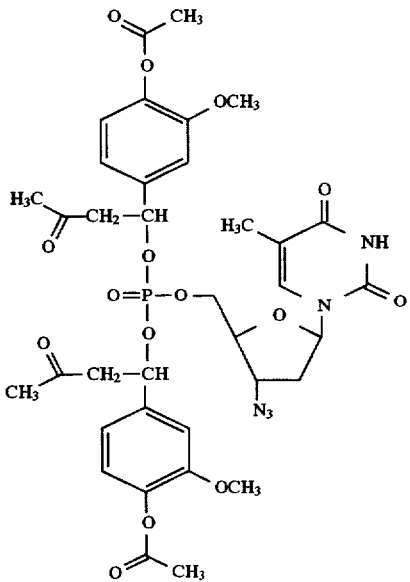

FORMULA 12

Method A

Ten mMoles of phosphorous trichloride and 10 mMoles of triethylamine are added to 50 ml of anhydrous diethyl ether at −78° C. Then 10 mMoles of 3'azido-2', 3'deoxythymidine (AZT) in 30 ml of anhydrous ether is added to the rapidly stirred solution. After 4 hours an additional 20 mMoles of triethylamine and 35 mMoles of anhydrous 4-(4-acetoxy,-3-methoxyphenyl), 4-hydroxy,2-butanone are added. After 6 hours the precipitated triethylamine hydrochloride is removed by filtration. Then 40 ml of water is slowly added. The organic phase is then separated and the solvent removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water. The desired prodrug (Formula 19) is then purified by crystallization from a suitable solvent or via chromatography on silica using routine methods.

Method B

Tem mMoles of phosphorous trichloride and 10 mMoles of triethylamine are added to 50 ml of anhydrous diethyl ether at −78° C. Then 10 mMoles of AZT in 50 ml of anhydrous ether is added to the rapidly stirred solution. After 2 hours 40 mMoles of diisopropylamine is added and the mixture is warmed to room temperature for 3 hours. Then 30 mMoles of strictly anhydrous 4-(4-acetoxy,3-methoxyphenyl), 4-hydroxy,2-butanone and 90 mMoles of 1-H-tetrazole are added. After 2 hours at room temperature the precipitated triethylamine hydrochloride and diisopropylamine hydrochloride are removed by filtration. Then the solvent is removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 100 ml×3 of water. The desired prodrug can then be purified by crystallization from a suitable solvent or via chromatography on silica.

Method C

Ten mMoles of phosphorous oxychloride and 10 mMoles of triethylamine are added to 50 ml of anhydrous diethyl ether at 30° C. Then 10 mMoles of AZT in 50 ml of anhydrous ether is added to the rapidly stirred solution. After 4 hours an additional 20 mMoles of triethylamine, 20 mMoles of n-methylimidazole, and 20 mMoles of 1-hydroxybenzotriazole and 35 mMoles of strictly anhydrous 4-(4-acetoxy,3-methoxyphenyl), 4-hydroxy,2-butanone are added. After 6 hours the precipitated triethylamine hydrochloride is removed by filtration. Then 200 ml of methylene chloride and 100 ml of water are added. The organic phase is separated, washed times 3 with 100 ml of 1M aqueous sodium bicarbonate followed by 50 ml×3 of water. The desired prodrug purified by crystallization from a suitable solvent or via chromatography on silica.

Method D

Ten mMoles of phosphorous oxychloride and 10 mMoles of triethylamine are added to 50 ml of anhydrous diethyl ether at 30° C. Then 10 mMoles of AZT in 50 ml of anhydrous ether is added to the rapidly stirred solution. After 4 hours the precipitated triethylamine hydrochloride is removed by filtration. Then 20 mMoles of the lithium alkoxide derivative of 4-(4-acetoxy,3-methoxyphenyl), 4-hydroxy,2-butanone in 50 ml of anhydrous diethyl ether is added at −78° C. under an inert atmosphere. After 6 hours the temperature is increased to room temperature for 2 hours. Then 100 ml of water is slowly added at 0° C. Then 200 ml of methylene chloride is added. The organic phase is then separated and washed times three with 100 ml of 1M aqueous ammonium chloride solution and washed times 4 with 100 ml of 1M aqueous sodium bicarbonate, followed by 100 ml×two of water, followed by 100 ml of saturated aqueous sodium chloride. The organic phase is dried with magnesium sulfate and the solvent is removed exvacuo. The desired prodrug can then be purified from the residue by flash chromatography on silica or by recrystallization from a suitable solvent.

Method E

Ten mMoles of phosphorous oxychloride and 30 mMoles of triethylamine and 30 mMoles of 3-nitro,1,2,4-triazole are added to 50 ml of anhydrous diethyl ether at room temperature. After 1 hour 10 mMoles of AZT in 20 ml of anhydrous ether is added to the rapidly stirred solution. After 4 hours 35 mMoles of strictly anhydrous 4-(4-acetoxy,3-methoxyphenyl), 4-hydroxy,2-butanone are added. After 6 hours the precipitated triethylamine hydrochloride is removed by filtration. Then 200 ml of methylene chloride and 100 ml of water are added. The organic phase is separated, washed times 3 with 50 ml of 1M aqueous sodium bicarbonate followed by 50 ml×3 of water. The desired is then prodrug purified by crystallization from a suitable solvent or via chromatography on silica.

Prodrugs for 2',3'-didehydro-2', 3'dideoxythymidine-5'monophosphate

2',3'-didehydro-2', 3'dideoxythymidine (D4T) is a potent inhibitor of HIV replication with a lower toxicity for myeloid progenitor cells the AZT. Martin, J. C. et al., *Nucleosides and Nucleotides*, 8:841 (1989). Antiviral activity requires conversion to the 5'triphosphate. The present prodrug method can be employed to facilitate the delivery of D4T-phosphate into cells an into the brain. An example of a prodrug for D4T-phosphate is shown below as Formula 13:

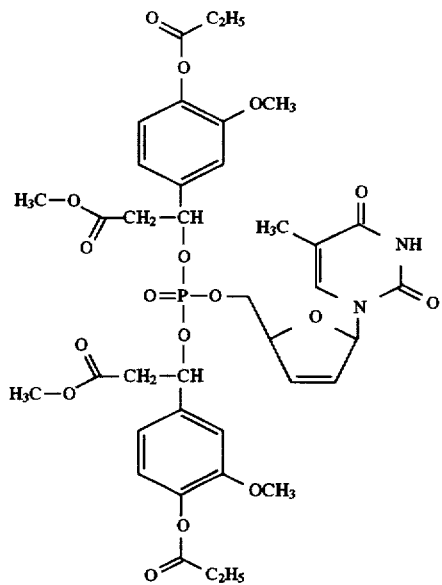

FORMULA 13

Synthesis of Formula 13

Formula 13 can be synthesized by the same methods described above for the synthesis of prodrugs for AZT except that 2',3'-didehydro-2',3'dideoxythymidine (D4T) is used in place of AZT and ethyl 3-hydroxy-3-(4-acetoxyphenyl)propionate is used in place of 4-(4-acetoxy, 3-methoxyphenyl), 4-hydroxy,2-butanone.

Prodrugs for 2',3'-dideoxyadenosine 5'monophosphate

The present prodrug method can be employed to deliver 2'3'dideoxyadenosine 5'monophosphate into the cytoplasm of cells. This compound is selectively toxic for TDT+ leukemia cells including those leukemic cells that are deficient in the kinase required for the phosphorylation of 2'3'dideoxyadenosine to the corresponding 5'phosphate. The structure of a prodrug for 2'3'dideoxyadenosine 5'monophosphate is shown below as Formula 14

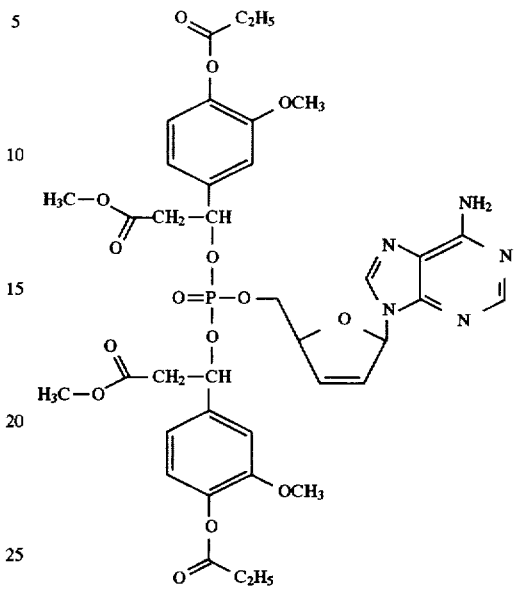

FORMULA 14

Synthesis of Formula 14

Method A

Ten mMoles of phosphorous trichloride and 10 mMoles of triethylamine are added to 50 ml of anhydrous diethyl ether at −78° C. Then 10 mMoles of 2',3'dideoxyadenosine in 30 ml of anhydrous ether is added to the rapidly stirred solution. After 4 hours an additional 20 mMoles of triethylamine and 35 mMoles of anhydrous 4-(4-acetoxy,3-methoxyphenyl), 4-hydroxy,2-butanone are added. After 6 hours the precipitated triethylamine hydrochloride is removed by filtration. Then 40 ml of water is slowly added. The organic phase is then separated and the solvent removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water. The desired prodrug is then purified by crystallization from a suitable solvent or via chromatography on silica.

Method B

Ten mMoles of phosphorous trichloride and 10 mMoles of triethylamine are added to 50 ml of anhydrous diethyl ether at −10° C. Then 10 mMoles of N-6-phthaloyl, 2',3'dideoxyadenosine in 30 ml of anhydrous ether is added to the rapidly stirred solution. After 4 hours an additional 20 mMoles of triethylamine and 35 mMoles of anhydrous 4-(4-acetoxy,3-methoxyphenyl), 4-hydroxy,2-butanone are added. After 6 hours the precipitated triethylamine hydrochloride is removed by filtration. Then 40 ml of water is slowly added. The organic phase is then separated and the solvent removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water. Then the solvent is removed exvacuo. The residue is dissolved in 90 ml of pyridine to which is added 30 ml of glacial acetic acid and 150 mMoles of hydrazine monohydrate. After 1 minute at room temperature the residue is taken up in 300 ml of methylene chloride. Then 100 ml of water is added. The organic phase is then separated and washed times 4 with 100 ml of 1M aqueous sodium bicarbonate, followed by 100 ml times two of water, followed by 100 ml of saturated aqueous sodium chloride. The organic phase is dried with magnesium sulfate and the solvent is removed exvacuo. The desired prodrug (Formula 21) can then be purified from the residue by flash chromatography on silica or by recrystallization from a suitable solvent.

Method C

Ten mMoles of phosphorous trichloride and 10 mMoles of triethylamine are added to 50 ml of anhydrous diethyl ether at −78° C. Then 10 mMoles of 2',3'dideoxyadenosine in 50 ml of anhydrous ether is added to the rapidly stirred solution. After 2 hours 40 mMoles of diisopropylamine is added and the mixture is warmed to room temperature for 3 hours. Then 30 mmoles of strictly anhydrous 4-(4-acetoxy, 3-methoxyphenyl), 4-hydroxy,2-butanone and 90 mMoles of 1-H-tetrazole are added. After 2 hours at room temperature the precipitated triethylamine hydrochloride and diisopropylamine hydrochloride are removed by filtration. Then the solvent is removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water, followed by 100 ml of saturated aqueous sodium chloride. The organic phase is dried with magnesium sulfate and the solvent is removed exvacuo. The prodrug is then purified by crystallization from a suitable solvent or via chromatography on silica.

Method D

Ten mmoles of phosphorous trichloride and 10 mMoles of triethylamine are added to 50 ml of anhydrous diethyl ether at −10° C. Then 10 mMoles of N6-phthaloyl-2',3'dideoxyadenosine in 50 ml of anhydrous ether is added to the rapidly stirred solution. After 2 hours 40 mMoles of diisopropylamine is added and the mixture is warmed to room temperature for 3 hours. Then 30 mMoles of strictly anhydrous 4-(4-acetoxy,3-methoxyphenyl), 4-hydroxy,2-butanone and 90 mMoles of 1-H-tetrazole are added. After 2 hours at room temperature the precipitated triethylamine hydrochloride and diisopropylamine hydrochloride are removed by filtration. Then the solvent is removed exvacuo. The residue is then treated with 30 ml of a solution containing 450 mg of iodine in a 2:1 tetrahydrofuran-water mixture at 0° C. for 5 minutes. Then 200 ml of methylene chloride and 100 ml of water are added. The organic phase is separated, washed times 3 with 50 ml of a 5% solution of aqueous sodium thiosulfate, followed by 50 ml×3 of water. The solvent is then removed exvacuo. The residue is dissolved in 90 ml of pyridine to which is added 30 ml of glacial acetic acid and 150 mMoles of hydrazine monohydrate. After 1 minute at room temperature 300 ml of methylene chloride is added. Then 100 ml of water is added. The organic phase is then separated and washed times 4 with 100 ml of 1M aqueous sodium bicarbonate, followed by 100 ml times two of water, followed by 100 ml of saturated aqueous sodium chloride. The organic phase is dried with magnesium sulfate and the solvent is removed exvacuo. The desired prodrug (Formula 21) can then be purified from the residue by flash chromatography on silica or by recrystallization from a suitable solvent.

Method E

Ten mMoles of phosphorous oxychloride and 10 mMoles of triethylamine are added to 50 ml of anhydrous diethyl ether at 30° C. Then 10 mMoles of 2',3'dideoxyadenosine in 50 ml of anhydrous ether is added to the rapidly stirred solution. After 4 hours an additional 20 mMoles of triethylamine, 20 mMoles of n-methylimidazole, and 20 mMoles of 1-hydroxybenzotriazole and 35 mMoles of strictly anhydrous 4-(4-acetoxy,3-methoxyphenyl), 4-hydroxy,2-butanone are added. After 6 hours the precipitated triethylamine hydrochloride is removed by filtration. Then 200 ml of methylene chloride and 100 ml of water are added. The organic phase is separated, washed times 3 with 50 ml of 1M aqueous sodium bicarbonate followed by 50 ml×3 of water. The desired prodrug is then purified by crystallization from a suitable solvent or via chromatography on silica.

Method F

Ten mMoles of phosphorous oxychloride and 10 mMoles of triethylamine are added to 50 ml of anhydrous diethyl ether at 30° C. Then 10 mMoles of N6-phthaloyl 2',3'dideoxyadenosine in 50 ml of anhydrous ether is added to the rapidly stirred solution. After 4 hours an additional 20 mMoles of triethylamine, 20 mMoles of n-methylimidazole, and 20 mMoles of 1-hydroxybenzotriazole and 35 mMoles of anhydrous 4-(4-acetoxy,3-methoxyphenyl), 4-hydroxy,2-butanone are added. After 6 hours the precipitated triethylamine hydrochloride is removed by filtration. Then 200 ml of methylene chloride and 100 ml of water are added. The organic phase is separated, washed times 3 with 50 ml of 1M aqueous sodium bicarbonate followed by 50 ml×3 of water. Then the solvent is removed exvacuo. The residue is dissolved in 90 ml of pyridine to which is added 30 ml of glacial acetic acid and 150 mMoles of hydrazine monohydrate. After 1 minute at room temperature the residue is taken up in 300 ml of methylene chloride. Then 100 ml of water is added. The organic phase is then separated and washed times 4 with 100 ml of 1M aqueous sodium bicarbonate, followed by 100 ml times two of water, followed by 100 ml of saturated aqueous sodium chloride. The organic phase is dried with magnesium sulfate and the solvent is removed exvacuo. The desired prodrug (Formula 21) can then be purified from the residue by flash chromatography on silica or by recrystallization from a suitable solvent.

Method G

Ten mMoles of phosphorous oxychloride and 30 mMoles of triethylamine and 30 mmoles of 3-nitro,1,2,4-triazole are added to 50 ml of anhydrous diethyl ether at room temperature. After 1 hour 10 mMoles of N6-phthaloyl-2',3'dideoxyadenosine in 20 ml of anhydrous ether is added to the rapidly stirred solution. After 4 hours 35 mMoles of strictly anhydrous 4-(4-acetoxy,3-methoxyphenyl), 4-hydroxy,2-butanone are added. After 6 hours the precipitated triethylamine hydrochloride is removed by filtration. Then 200 ml of methylene chloride and 100 ml of water are added. The organic phase is separated, washed times 3 with 50 ml of 1M aqueous sodium bicarbonate followed by 50 ml×3 of water. The solvent is then removed exvacuo. The residue is dissolved in 90 ml of pyridine to which is added 30 ml of glacial acetic acid and 150 mMoles of hydrazine monohydrate. After 1 minute at room temperature 300 ml of methylene chloride is added. Then 100 ml of water is added. The organic phase is then separated and washed times 4 with 100 ml of 1M aqueous sodium bicarbonate, followed by 100 ml times two of water, followed by 100 ml of saturated aqueous sodium chloride. The organic phase is dried with magnesium sulfate and the solvent is removed exvacuo. The desired prodrug (Formula 21) can then be purified from the residue by flash chromatography on silica or by recrystallization from a suitable solvent.

Treatment with and Administration of the Prodrugs

The present prodrugs can be used to treat certain disorders by allowing the penetration of the drug through the blood brain barrier and into cells by converting them into lipid-soluble compounds. The prodrugs then undergo biotransformation, in vivo yielding the active phosphorylated form of the drug which is necessary for the treatment of the disorder. For example the prodrugs described for AZT-monophosphate, D4T-monophosphate, PMEA, and 2'3'dideoxyadenosine-monophosphate can be administered to a patient with Acquired Immunodeficiency Syndrome or HIV infection. The prodrugs for PMEA can be administered to a patient with a herpes infection. The prodrugs for 2'3'dideoxyadenosine-monophosphate can be administered to a patient with TDT+leukemia. The prodrugs will then be metabolized in vivo the active phosphorous bearing drugs. The treatment program, i.e., drug dosage, frequency of administration, and length of administration will depend upon several factors such as the age, weight, and physical condition of the patient, the stage of the disease and the patients tolerance for the drug.

The prodrugs can be administered orally, parenterally or topically. The form in which the drugs are given (e.g., powder, tablet, capsule, solution, emulsion) will depend upon the route by which it is to be administered. The quantity of the drugs to be administered will be determined on an individual basis and will be determined in part on consideration of the individuals size, the severity of the symptoms, and the result sought. The composition of the present invention can optionally include, in addition to the prodrug other components. The other components included in a particular composition are determined primarily by the route of administration. For example, a composition to be administered orally in tablet form can include, in addition to the drug, a filler (e.g., lactose), a binder (e.g. carboxy-methyl cellulose, gum arabic, gelatin) a flavoring agent, a coloring agent, and a coating material (e.g., wax, or a plasticizer). A composition to be administered in a liquid form can include the drugs of the present invention, and optionally an emulsifying agent, a carrier (e.g. saline or water), a flavoring agent, and or a coloring agent. A composition to be administered in a topical form can include an emulsifying agent, a solvent, stabilizing agents and a base such as polyethylene glycolic or carbopol.

EXAMPLES

Example 1

A Prodrug for 3'azido-3'deoxythymidine 5'phosphate

The prodrug method was employed to synthesize a neutrally charged, lipophilic prodrug for the 3'azido-3'deoxythymidine 5'phosphate. The resulting prodrug was an extremely potent inhibitor of the AIDS virus and hepatitis B in vitro. The structure of this prodrug is shown below as structure 5:

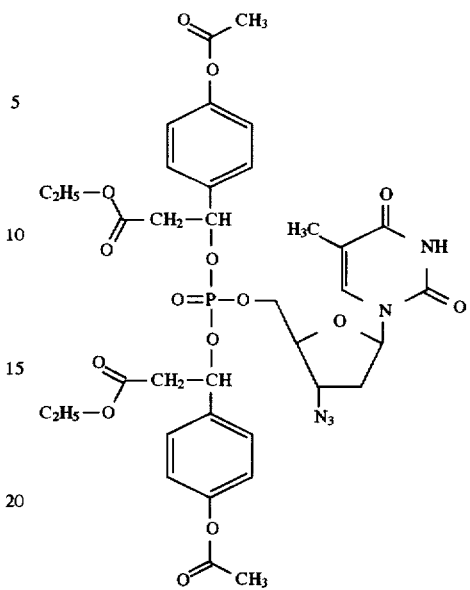

STRUCTURE 5

Synthesis of a Prodrug for AZT

The prodrug for AZT shown in Structure 5 was synthesized by the reaction of AZT with the compound shown below as Structure 6 in the presence of 1-H-tetrazole followed by oxidation with 3-chloroperoxybenzoic acid.

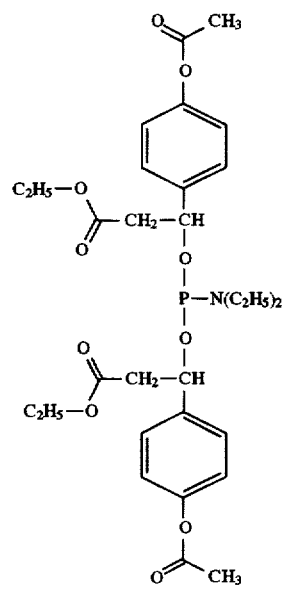

STRUCTURE 6

Synthesis of Intermediate given by Structure 6

A solution of freshly distilled diethylphosphoramidous dichloride (0.607 gm, 3.49 mMoles) was added to 5 ml of anhydrous diethyl ether under a dry nitrogen atmosphere and cooled to −20° C. A solution-of ethyl 3-hydroxy-3-(4-acetoxyphenyl)propionate (1.760 gm, 6.98 mMoles) and dry triethylamine (0.777 gms, 7.68 mMoles) in 50 ml of diethyl ether was added dropwise over 15 minutes. After stirring for 15 more minutes the external cooling was removed and the reaction mixture was stirred at room temperature for 20 hours. The triethylamine hydrochloride was then removed by filtration under a nitrogen atmosphere. Evaporation of the filtrate yielded 2.29 grams of a viscous oil. The oil was then dissolved in 100 ml of methylene chloride, and was washed at 4° C. with 50 ml of saturated aqueous saline, followed by 5% NaHCO$_3$ (50 ml×2), and 50 ml of water. The organic phase was then dried over sodium sulfate, filtered and dried exvacuo at room temperature. The result was 2.22 grams of a semi-solid gum. The product was unstable to silica chromatography and was employed without further purification in the next step. FAB mass spectroscopy and proton NMR were consistent with the product being that of the N,N diethylphosphoramidite shown in Structure 6.

Synthesis of the AZT Prodrug shown as Structure 5

Figure 2A:
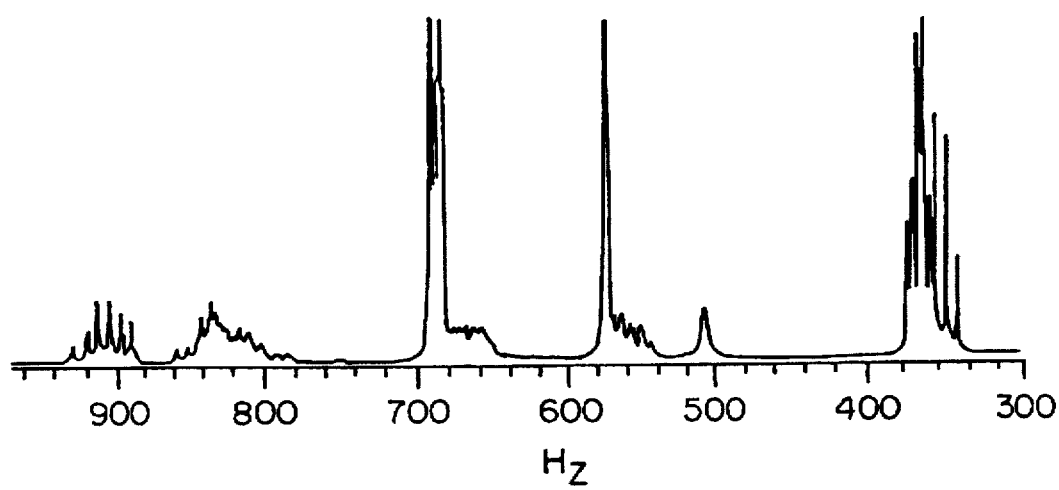
FIG. 2 is a graphic illustration of the 300 MHZ nuclear magnetic resonance (NMR) spectra of the AZT prodrug Structure 5.
Figure 2B:
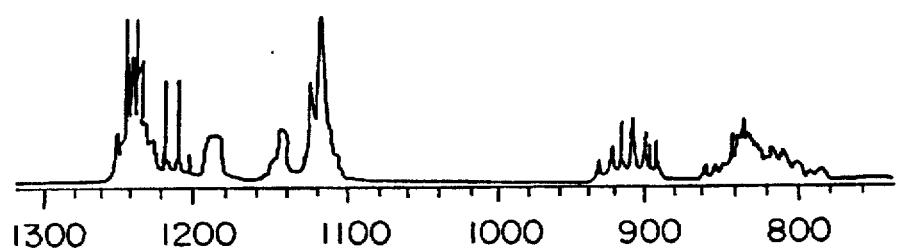
Figure 2C:
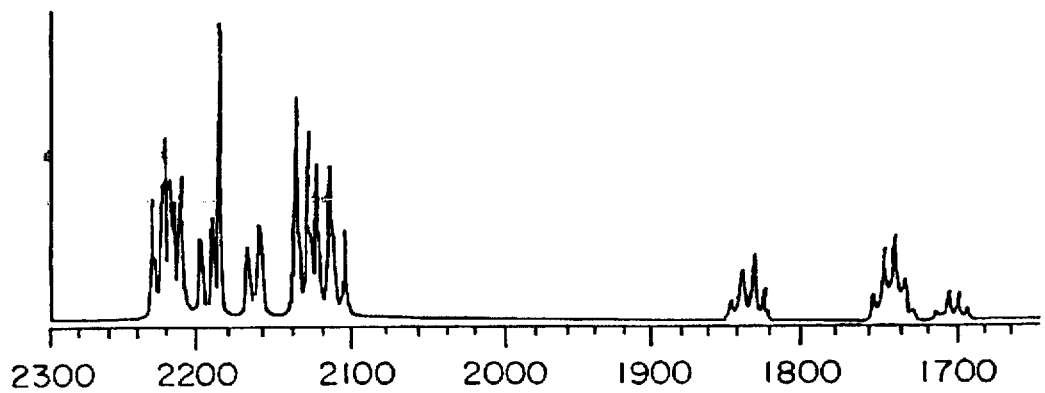

1-H-tetrazole (462 mg, 6.60 mMoles) was added to 2.00 grams of the N,N diethylphosphoramidite (Structure 6) and to 3'azido-3'deoxythymidine (707 mg, 2.63 mMoles) in 10 ml of anhydrous tetrahydrofuran. (The AZT provided by Aldrich contained 0.085 moles water per mole of AZT.) After 1.5 hours the solution was cooled to −40° C. and a solution of 3-chloroperoxybenzoic acid (873 mg, 4.3 mMoles as 85% reagent) in 15 ml of dry methylene chloride was added rapidly in a dropwise fashion. External cooling was removed and after 15 minutes, 20 ml of 10% aqueous NaHSO$_4$ was added and stirred vigorously for 10 minutes. The mixture was transferred to a separatory funnel with the addition of 50 ml of methylene chloride. Upon shaking an intractable emulsion was formed. After the addition of 500 ml of diethyl ether a clean phase separation was obtained. The organic phase was washed with 30 ml of 10% aqueous NaHSO$_4$, saturated NaHCO$_3$ (25 ml×2), and water (25 ml×2). The organic phase was then dried over sodium sulfate, filtered and dried exvacuo to yield 2.30 grams of crude product. The desired product was then purified by silica gel chromatography with CHCl$_3$/methanol 99:1 as eluant. 821 mg of product was obtained which was pure by TLC. NMR revealed a mixture of diastereomers. FAB mass spectroscopy revealed a molecular weight of 815.7 In an attempt to separate the d-l pair form the meso pair of isomers the sample was rechromatographed on a longer silica column and eluted with CHCl$_3$/methanol 99:1. This second chromatography was unsuccessful and complicated by the appearance of a hydrocarbon peak noted on NMR. This hydrocarbon peak was traced to a contaminant present in a commercially obtained reagent grade chloroform. The sample accordingly was subjected to a third chromatographic purification on a 3 inch silica column which was eluted with chloroform followed by CHCl$_3$/methanol 99:1. This removed all detectable traces of the hydrocarbon contaminant. 260 mg of product was isolated. This material was pure on TLC and by high field NMR. No AZT was noted on HPLC examination of a sample obtained after the first of the three chromatographic separation described above. The proton NMR revealed the presence of diastereomers. Two pairs of isomers were separated by HPLC on silica. However, attempts to further resolve the mixture were unsuccessful. p$^{31}$ NMR demonstrated that 2 phosphorous peaks in each mixture of diastereomers. The structure was further confirmed by proton NMR COSY analysis. High resolution mass spectrometry revealed a molecular weight of 815.2440 (+/−0.0043). This is in agreement with the calculated mass of 815.248. The 300 MHZ NMR is shown in FIG. 2.

Antiretroviral Activity of the Prodrug for AZT

The antiviral activity of the AZT prodrug was evaluated in the Retrovirus Research Laboratory at Southern Research Institute. The AZT prodrug (Structure 5) was tested against HIV in CEM cells in a standardized assay system. In this assay the CEM cells were grown in microtitre plates and incubated for 6 day with or without a HIV. The cells were incubated with prodrug or AZT at varying concentrations. After 6 days the percentage of viable cells was measured by employing a standardized assay based upon the conversion of a tetrazolium salt to a formazan chromaphore by viable cells. (T. Mossman, *J. Immunol. Methods*, 65:55 (1983)). The production of the chromaphore was measured spectrophotometrically with a Molecular Devices Vmax plate reader at 570 nm. From the optical density data a computer program calculated the per cent reduction in viral cytopathic effect (CPE), the prodrugs cytotoxic effect, and IC$_{50}$ values.

The prodrug for AZT proved to be an extremely potent inhibitor of the AIDS virus as measured in this assay. The IC$_{50}$ value; defined as that concentration of drug inhibited the HIV induced CPE 50% was 24 nanomolar for the AZT prodrug. The TC$_{50}$ value; defined as that concentration of drug that resulted in a 50% reduction of cell viability in uninfected cells was 7800 nanomolar. When the prodrug was added to the cell cultures 8 hours prior to infecting with HIV the IC$_{50}$ for the prodrug was 5 nanomolar. The IC$_{90}$ for the prodrug was 10 nanomolar. The IC$_{50}$ for AZT under the same conditions was also 5 nanomolar. The IC$_{90}$ for AZT was 10 nanomolar.

Activity of the AZT Prodrug Against Hepatitis B

AZT triphosphate is a potent inhibitor of the hepatitis B DNA polymerase. However, in vitro and in vivo AZT has no significant antiviral activity against hepatitis B. Nordenfeld E. et al., *J. Med. Virology*, 22:231 (1987); Haritani, H. et al., *J. Med. Virology*, 29:244 (1989); Farraye, F. et al., *J. Med. Virology*, 29:266 (1989); Korba, B. et al., *Antiviral Res.*, 15:217 (1991). This is not surprising in view of the inability of liver cells to phosphorylate AZT. Cretton, E. et al., *Biochem. Pharm.*, 42:1475 (1991). The AZT prodrug was examined for activity against the hepatitis B virus in vitro using the assay system as described by Korba and Milman in *Antiviral Res.*, 15:217 (1991). AZT alone failed to inhibit virion production or the intracellular concentration of hepatitis B replicative intermediates even at 100 micromolar concentration. In contrast, the AZT prodrug at 33 micromolar concentration inhibited virion production by 97% and decreased the intracellular concentration of hepatitis B replicative intermediates by 91%. At 10 micromolar the AZT prodrug inhibited virion production by 82% and decreased the intracellular concentration of hepatitis B replicative intermediates by 50%. The AZT prodrug at 100 micromolar was nontoxic to the cells as determined by a neutral red dye uptake assay.

Lack of Anticholinesterase Activity of the AZT Prodrug

The AZT prodrug was evaluated for anticholinesterase activity at the Laboratory of Neurotoxicology and Pharmacology at Duke University using a well established acetylcholinesterase activity inhibition assay. Elleman et al., *Biochemical Pharmacology*, 7:88 (1962). The prodrug was tested for anticholinesterase activity in chicken brain homogenate and electric eel extract. No inhibition of acetylcholinesterase activity was noted at 10$^{-5}$M. The drug had no acute toxicity to mice when given intraperitoneally (IP) at a dose of 100 mg/kg as an emulsion in 5% Emulphor EL 620. One mouse was given a dose of 300 mg/kg IP without evident acute toxicity during a 24 hour period of observation.

Example 2
A Prodrug for PMEA

PMEA (9-(2-phosphonylmethoxy-ethyl)adenine) is a potent antiviral agent which is active against a wide variety of viruses including: HIV, herpes simplex, and CMV. De Clercq, E. D. et al., *Antiviral Research*, 8:261 (1987); Gangemi, J. D. et al., *Antimicrobial Agents and Chemotherapy*, 33:1864 (1989); De Clercq, E. D. et al., *Antimicrobial Agents and Chemotherapy*, 33:185 (1989); Balzarini, J. et al., *Proc. Natl. Acad. Sci.* (USA), 86:332 (1989). However, PMEA is negatively charged and penetrates into cells and across biological membranes very poorly. Numerous attempts have been made to prepare lipophilic prodrugs for PMEA. Acyloxyalkyl prodrugs of PMEA do not display significantly enhanced activity against the AIDS virus. Starrett, J. E. et al., *Antiviral Research*, 19:267 (1992). Bis phosphoesters of 2,2'dithioethanol are highly effective prodrugs in vitro. Puech, F. et al., *Antiviral Research*, 22:155 (1993). However, the metabolism of these prodrugs generates 2 mole equivalents of ethylene sulfide which is extremely toxic.

The present prodrug method was employed to synthesize a neutrally charged prodrug for PMEA which is highly effective. The structure of this prodrug is shown below as Structure 7:

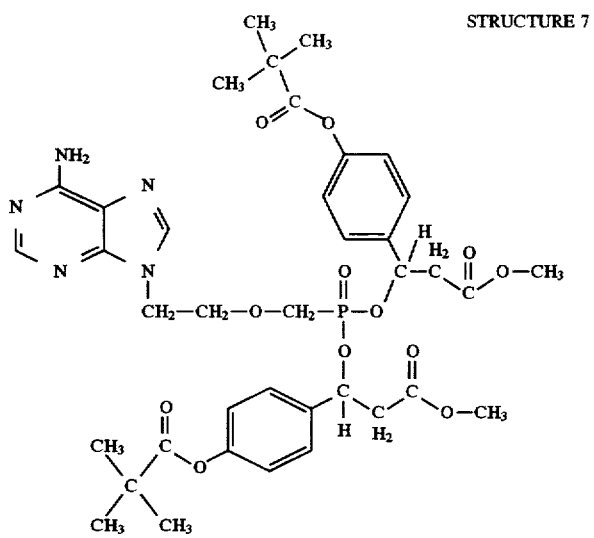

STRUCTURE 7

Synthesis of PMEA Prodrug of Structure 7

PMEA 9-(2-phosphonylmethoxy-ethyl) adenine (PMEA) was provided by Antonin Holy and synthesized by published routes.

Methyl 4-Hydroxybenzoylacetate

A solution of 4-hydroxyacetophenone (500 g) in DMF (1.5 L) was slowly added to a suspension of sodium hydride (331 g) in DMF. The mixture was stirred for 15 min. till gas evolution had subsided. Dimethyl carbonate (1.55 L) was added and the reaction stirred overnight at room temperature. The reaction was worked up by pouring into ice (15 LB) followed by acidification to pH 2 with hydrochloric acid. The aqueous mixture was extracted with ethyl acetate (3×5 L) and this was washed with water (3×1 L) and brine, then dried (Na$_2$SO$_4$), filtered, and concentrated. The crude product was purified by chromatography on silica gel (10 Kg) with 15 to 40% ethyl acetate-hexane. The chromatographed product was recrystallized twice from ethyl acetate-hexane to yield 313 gm first crop material as a white powder with mp 90°–92° C.

Purity by HPLC was 99.9%. NMR (CDC13)—3.76 (s, 3H), 3.99 (s, 2H), 6.90 (d, 2H), 7.18 (s, 1H), 7.86 (d, 2H). Elemental analysis; calculated for C: 61.86, H: 5.19, 0:32.95. Found C: 62.00, H: 5.20, 0: 32.98.

Methyl 3-Oxo-3-(4-Pivaloyloxyohenyl) Propionate

Ten gm. of methyl 4-hydroxybenzoylacetate (0.05 moles), triethylamine 8.0 ml (0.057 moles) and 100 mg of dimethylaminopyridine were added to 100 ml of anhydrous CH$_2$Cl$_2$ under argon. Then with ice cooling pivaloyl chloride (0.05 moles) was added over 10 minutes. After the addition was completed the ice bath was removed and the reaction was stirred for 2.5 hours. Water was then added and the reaction stirred overnight. The reaction mixture was then washed with H$_2$O (100 ml×2), 5% aqueous citric acid (50 ml×3), Saturated aqueous NaHCO$_3$ (100 ml×1), and dried with Na$_2$SO$_4$. The solvent was then removed on a rotovap to yield 14 gm of a golden colored oil which gave a single spot on silica TLC with chloroform: methanol (15:1.)

Methyl 3-Hydroxy-3-(4-Pivaloyloxyphenyl) Propionate

Methyl 3-Oxo-3-(4-Pivaloyloxyphenyl) Propionate 14 gm (0.05 moles) was dissolved in 100 ml of ethanol. After equilibrating with argon, 500 mg of 10% Pd on carbon (Aldrich) was added. The argon was then removed exvacuo and the mixture hydrogenated at 40 PSI at room temperature on a Parr hydrogenation apparatus. The progress of the reaction was monitored by TLC The reaction was completed after 6.5 hours. The mixture was then filtered and the solvent removed exvacuo to yield 13 gm (93% yield) of a white crystalline powder. NMR: (CDC13) 7.0 (d,2H), 7.2 (d, 2H), 5.17(q, 1H), 3.7 (s, 3H), 2.92 (m, 1H), 2.73 (m, 2H), 1.35(s 9H).

Figure 3A:
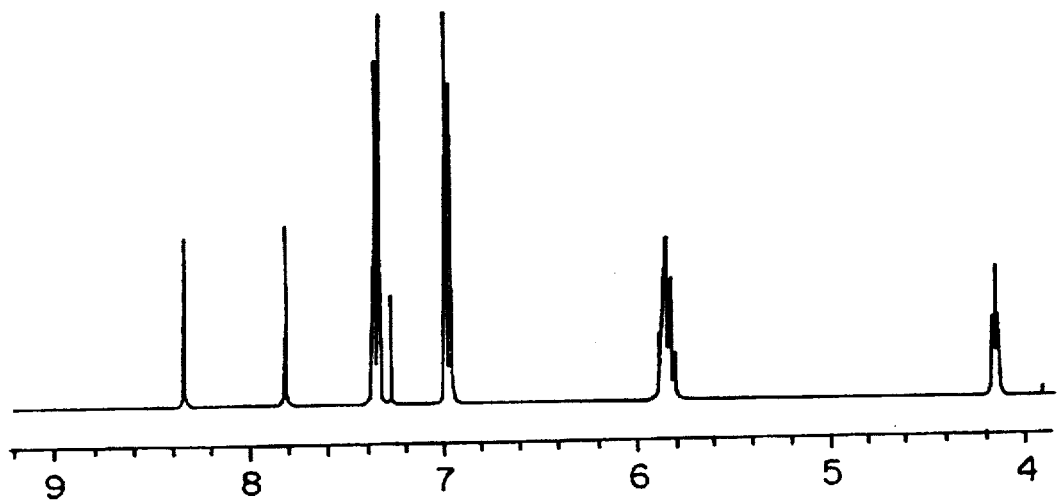
FIG. 3 is the 300 MHZ nuclear magnetic resonance (NMR) spectra of the PMEA prodrug Structure 7A.
Figure 3B:
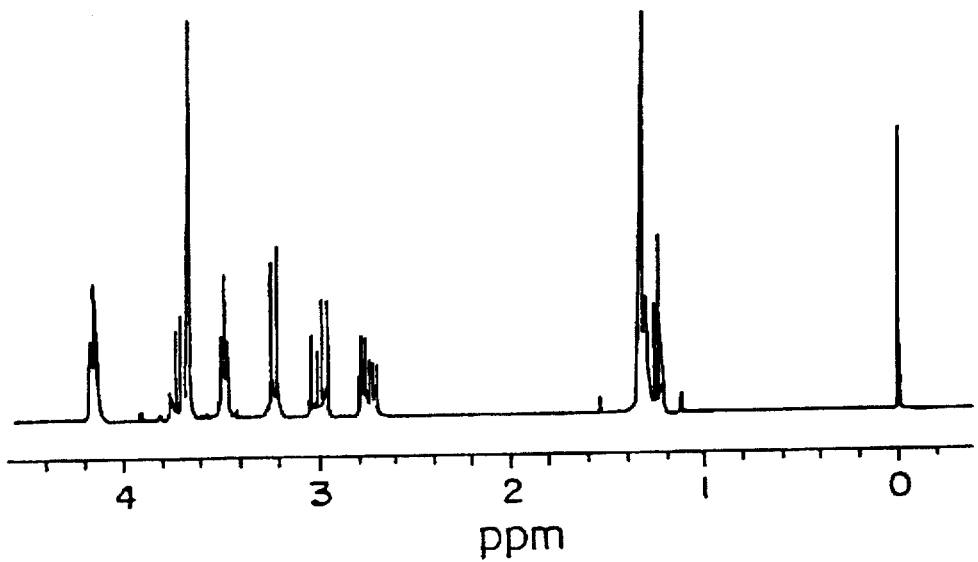
Figure 4A:
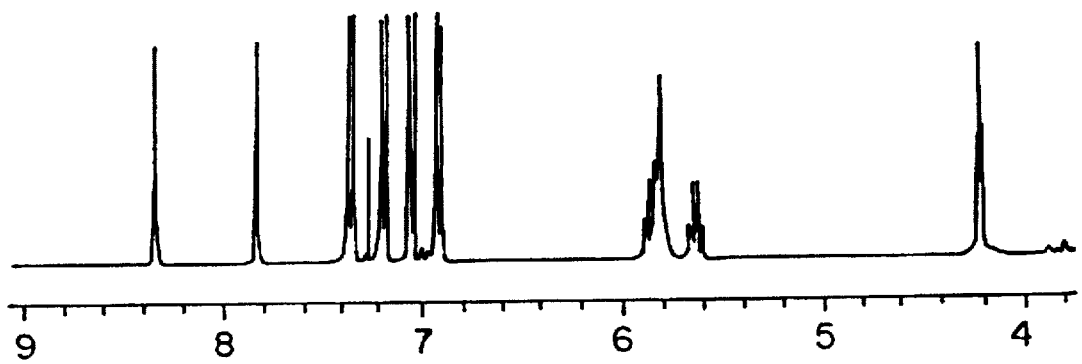
FIG. 4 is the 300 MHZ nuclear magnetic resonance (NMR) spectra of the PMEA prodrug Structure 7B.
Figure 4B:
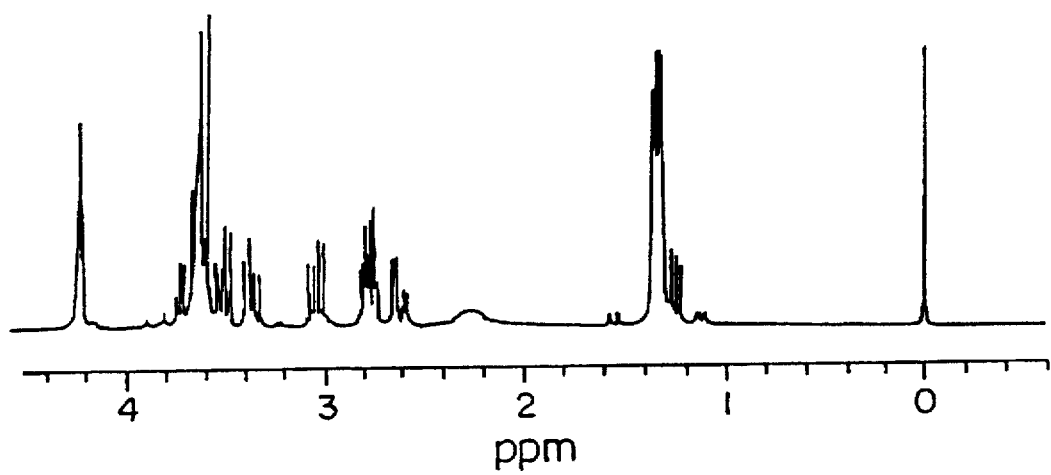
Figure 5A:
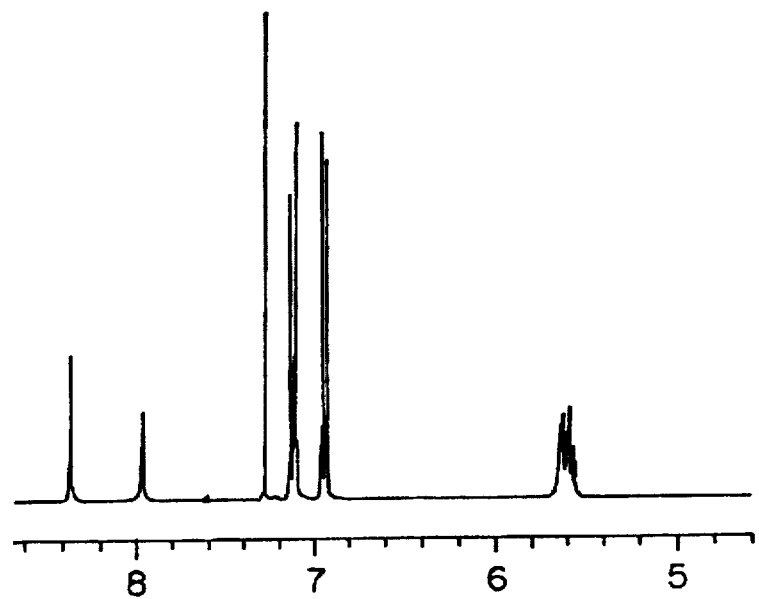
FIG. 5 is the 300 MHZ nuclear magnetic resonance (NMR) spectra the PMEA prodrug Structure 7C.
Figure 5B:
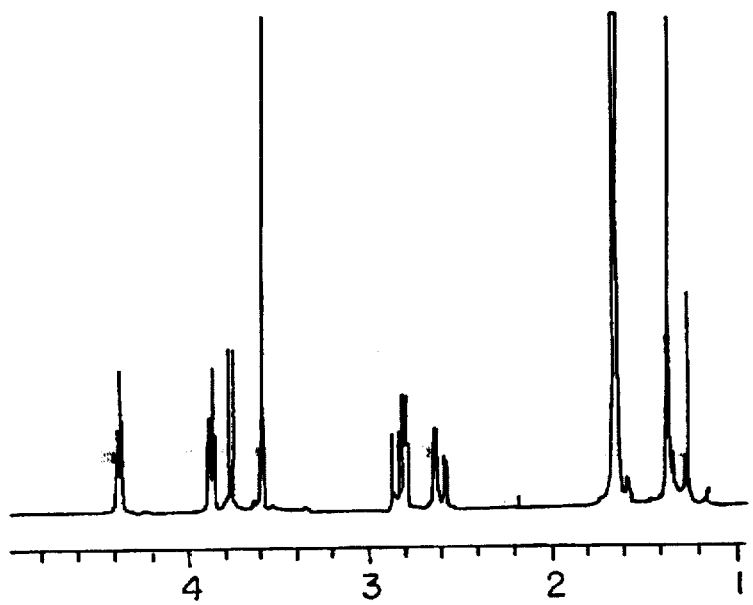

PMEA 3.0 gm (0.011 moles) was refluxed under argon with 15 ml of 1,1dichloromethyl ether for 24 hours to yield a bright orange-yellow precipitate. The dichloromethyl ether was removed by filtration and the precipitate washed under anhydrous conditions with 40 ml×4 of toluene and dried exvacuo. Then 20 ml of anhydrous CH$_2$Cl$_2$, 0.02 moles of triethylamine, 0.03 moles of N-methylimidazole, and 0.02 moles of methyl 3-hydroxy-3-(4-pivaloyloxyphenyl) propionate was added under argon with ice cooling. The reaction mixture was then sonicated with an ACE 600 watt ultrasonicator with a 0.25 inch probe at 35% maximum power, with an on:off pulse cycle of 2 sec on: 1 sec. off. Ultrasonication was stopped after 30 minutes and the reaction mixture was allowed to sit at room temperature overnight. The mixture was then filtered, concentrated exvacuo and applied to a silica column and eluted with 1 liter of chloroform followed by chloroform: methanol 15:1. An oil 4.0 grams containing the product was isolated. Contaminating triethylamine was removed by washing with 5% aqueous citric acid followed by repeat silica gel chromatography using chloroform: methanol: water, 15:1: 0.1 as eluant. Finally, the prodrug was purified by multiple runs on a Rainin C-18 Dynamax 60A preparative HPLC column at a flow rate of 10 ml/min. with acetonitrile: water 1:1. Two meso forms and a racemic mixture of stereoisomers were separated an examined by NMR and high resolution mass spectrometry. The yield of purified prodrug was 1.5 grams. Mass spectrometry was similar for all three isolated fractions 7-a, 7-b, 7-c with M+H of 798.3121, 798.3113, and 798.3110. (expected 798.3115). Proton NMRs of prodrugs 7a–c are shown in FIGS. 3–5.

Antiviral Screening of PMEA Prodrugs 7: HIV

Antiviral activity of the prodrug was evaluated against HIV 1 in CEMSS cells in a standardized assay system. The CEM cells were grown in microtitre plates and incubated for 6 days with or without HIV. The cells were incubated with prodrug or PMEA at varying concentrations. After 6 days the percentage of viable cells was measured by employing an assay based upon the conversion of a tetrazolium salt to a formazan chromaphore by viable cells. The production of the chromaphore was measured spectrophotometrically at 570 nm. From the optical density data a computer program calculated the per cent reduction in viral cytopathic effect (CPE), the prodrugs cytotoxic effect, and EC50 values.

HSV and HCMV CPE Inhibition

Human low passage foreskin fibroblast cells were incubated with graded concentrations of the prodrug or PMEA with or without the respective virus in microtitre plates. Drug was added at the time of virus infection. The incubation time was three days for HSV and 14 days for HCMV. The cells were then stained with crystal violet and read on a Skatron Plate Reader at 620 nm. From the optical density data a computer program calculated the percent reduction in viral cytopathic effect (CPE), the prodrugs cytotoxic effect, and EC50 values. The viral strains employed were HSV1-E377, HSV-2-MS, HCMV-AD169. One thousand PFU/well of HSV virus or 2500 PFU/well of HCMV were employed in these assays.

HSV and HCMV Plaque Inhibition

Human low passage foreskin fibroblast cells were incubated with graded concentrations of the prodrug or PMEA with or without the respective virus in six well plates. 20–30 PFU of virus was added 1 hour prior to addition of the drug. The cells were incubated with an agarose MEM culture media and incubated for three days for HSV and 14 days for HCMV. The cells were then stained with neutral red and plaques counted using a stereomicroscope.

Hepatitis B

The PMEA prodrug was tested for its ability to inhibit hepatitis B viral replication by an in vitro assay as previously described by Korba. Chronically hepatitis B producing human hepatocyte (2.2.15 cells) were grown to confluence in microtitre wells. Test compounds were added daily for a 9 day period. The culture medium was changed daily and stored for quantitation of extracellular hepatitis B viral (HBV) DNA on days 0, 3, 6, and 10. On day 10 the cells were lysed and the intracellular HBV episomal monomeric DNA and HBV replicative intermediates (RI) were quantitated. Toxicity of test compounds was assayed by treating confluent monolayers of the hepatocyte with graded doses of the compound. Toxicity was determined by the uptake of neutral red dye as measured by absorbance at 510 nanometers relative to untreated cells 24 hours following day 9 of treatment.

Cytotoxicity Screening—Cell Count Assay

Human low passage foreskin fibroblast cells were incubated with graded concentrations of the prodrug or PMEA in six well plates which had been seeded 24 hours earlier at a concentration of $2.5 \times 10^4$ cells per well. After three days the cells were trypsinized and counted on a Coulter Counter.

Neutral Red Assay

Human low passage foreskin fibroblast cells were incubated with graded concentrations of the prodrug or PMEA in six well plates which had been seeded 24 hours earlier at a concentration of $2.5 \times 10^4$ cells per well. After 7 days the cells were incubated 1 hour with 0.01% neutral red and after washings the optical densities are read at 550 nm on a plate reader. From the optical density data a computer program calculated the prodrugs cytotoxic effect.

Results

The three isomeric fractions of prodrug 7 were highly active antiviral agents. The toxicity of prodrugs 7-a, 7-b, and 7-c were all similar. However, antiviral activity varied significantly between the different diastereomers. The data is summarized in the tables below:

Antiviral Activity of PMEA Prodrug 7-a

| Viral Assay | Prodrug EC50 | PMEA EC50 | Prodrug CC50 | PMEA CC50 | Prodrug CC50/EC50 | Prodrug Potency |
|---|---|---|---|---|---|---|
| HIV 1 CPE | .32* | >20 | 2.4 | >20 | 7.5 | >62.5 |
| HSV1 CPE | .06 | 68.5 | 76 | >366 | 1266 | 1140 |
| HSV2 CPE | 0.58 | >366 | 76 | >366 | 131 | >630 |
| HSV1 Plaque | 2.25 | 52 | >125 | >366 | >55 | >23 |
| HSV2 Plaque | 4.4 | 215 | >125 | >366 | >28 | 48 |
| HCMV Plaque | 3.1 | 12.4 | 19 | >366 | 6 | 4 |
| HBV Virion | 1.6 | 4.3 | 587 | 235 | 366 | 2.7 |
| HBV RI* | 3.0 | 8.2 | 587 | 235 | 195 | 2.7 |

Antiviral Activity of PMEA Prodrug 7-b

| Viral Assay | Prodrug EC50 | PMEA EC50 | Prodrug CC50 | PMEA CC50 | Prodrug CC50/EC50 | Prodrug Potency |
|---|---|---|---|---|---|---|
| HIV 1 CPE | .006* | >20 | .85 | >20 | 141 | >33005 |
| HSV1 CPE | .63 | 68.5 | 52.9 | >366 | 84 | 109 |
| HSV2 CPE | 2.6 | >366 | 52.9 | >366 | 20 | >140 |
| HSV1 Plaque | 2.0 | 52 | >125 | >366 | >62 | 26 |
| HSV2 Plaque | 1.5 | 215 | >125 | >366 | >83 | 143 |
| HCMV Plaque | >6 | 12.4 | 11 | >366 | — | 2 |
| HBV Virion | 2.6 | 4.3 | 359 | 235 | 90 | 1.6 |
| HBV RI* | 4.5 | 8.2 | 359 | 235 | 103 | 1.8 |

Antiviral Activity of PMEA Prodrug 7-c

| Viral Assay | Prodrug EC50 | PMEA EC50 | Prodrug CC50 | PMEA CC50 | Prodrug CC50/EC50 | Prodrug Potency |
|---|---|---|---|---|---|---|
| HIV 1 CPE | .015 | >20 | 0.98 | >20 | 65 | >1300 |
| HSV1 CPE | .00125 | 68.5 | 32 | >366 | 25,600 | 54,800 |
| HSV2 CPE | 0.14 | >366 | 32 | >366 | 228 | >2614 |
| HSV1 Plaque | 1.2 | 52 | >125 | >366 | >104 | 43 |
| HSV2 Plaque | 1.6 | 215 | >125 | >366 | >78 | 134 |
| HCMV Plaque | 2.9 | 12.4 | 11 | >366 | 3.8 | 4.3 |
| HBV Virion | 0.5 | 4.3 | 418 | 235 | 836 | 8.6 |
| HBV RI* | 0.9 | 8.2 | 418 | 235 | 464 | 9 |

*Inactive against HIV in ⅓ trials
Concentrations are micromolar
EC50 = concentration which inhibits virus effect 50%
CC50 = concentration which is 50% cytotoxic
Prodrug Potency = EC50 for PMEA/EC50 for prodrug
HBV RI = Hepatitis B Replicative Intermediates*
CPE = cytopathic effect

| Toxicity of Prodrugs in Proliferating Human Foreskin Cells | | |
|---|---|---|
| Drug | Cell Count Assay CC50 | Neutral Red Assay CC50 |
| PMEA | 104 | — |
| Prodrug B1 | 6 | 40.06 |
| Prodrug B2 | 5 | 22 |
| Prodrug B3 | 5.5 | 39.5 |

Concentrations are micromolar

Prodrug Stability

Prodrug A was dissolved in solutions buffered to pH 2.0, 7.0, and 9.0 using boric acid, citric acid, sodium phosphate based buffers at room temperature. Prodrug decomposition was monitored by thin layer chromatography on silica plates developed with chloroform: methanol, 8:1. UV detection was employed. No decomposition was detected at 4 hours. At 14 hours slight decomposition was noted at pH 2 and pH 9. At 42 hours slight decomposition was noted at pH 7. At pH 2 and pH 9 more then 50% decomposition had occurred at 42 hours. However, significant amounts of intact prodrug still remained.

Antiherpes Activity of the PMEA Prodrug 7C in Mice

The PMEA prodrug given by structure 7C was highly active in a mouse model of herpes virus type 1 vaginal infection when applied topically. Details are given below.

The PMEA prodrug was formulated into a hydrophilic water based cream containing 20% Emulphor-EL620, 5 mg/ml prodrug, and 50 mg/ml of Carbopol EX214. Control vehicle was prepared in a similar fashion but the prodrug was omitted.

Six week old Balb-C mice (10 mice/group) were infected on day 0 with a standardized inoculum of herpes virus type 1 via the vaginal route. After 24 hours treatment was initiated with 0.1 ml of prodrug cream or vehicle topically twice daily for 6 days. Viral titres of vaginal washing were assayed on days 1, 3, 5, 7 and 10.

Figure 6:
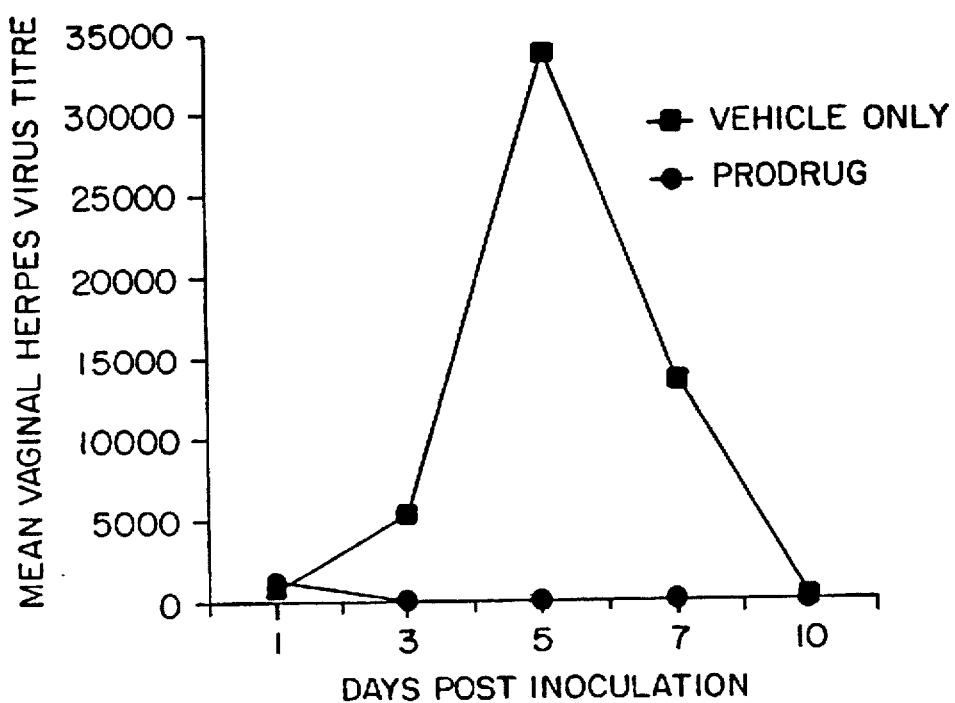
FIG. 6 is a graphic illustration of the viral titres in vaginal washings of mice infected with herpes virus type 1 and treated with PMEA prodrug or control vehicle.

The prodrug treated mice had a dramatic and sustained drop in viral titres as shown in FIG. 6.

Example 5
Synthesis and Delivery in Mice of a Fluorescent Phosphonate via the Prodrug Method We have employed the present prodrug approach to deliver in vivo a fluorescent model phosphonate compound shown below as Structure 8.

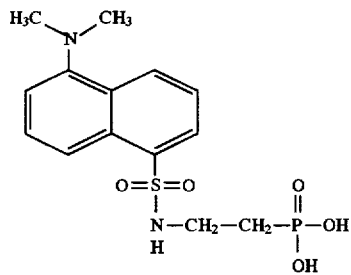

STRUCTURE 8

Synthesis of Structure 8

2-amino-ethylphosphonic acid (3.027 gm, 0.024 moles) was dissolved in 60 ml of water containing 1.22 gm of sodium hydroxide. Dansyl chloride (6.53 gm, 0.0242 moles) dissolved in 220 ml of acetonitrile was added with vigorous stirring. 0.5N sodium hydroxide solution was added dropwise to keep the pH 9–10 over the course of 1 hour. Then the acetonitrile was removed exvacuo and the aqueous phase was washed×3 with 70 ml of methylene chloride. 6N HCl was added to adjust the pH to 2. After filtering the solution was concentrated on a rotovap. Then 300 ml of boiling ethanol was added and the precipitate was removed by filtration. The ethanol was removed exvacuo to yield 8 gms of yellow fluorescent crystalline product which was again recrystallized from ethanol. NMR (DMSO) 300 MHZ 10–11 (broad peak, 2 H), 8.5 (d, 1H), 8.3 (d, 1H), 8.17 (d, 1H), 7.8 (t, 1H), 7.6 (m, 2H), 7.23 (d, 1H), 2.9 (m, 2H), 2.8 (s, 6H), 1.6 (m, 2H). Decoupled Phosphorus NMR should 1 peak.

The dansyl phosphonate given by Structure 8 was converted into prodrugs of the structures shown below as Structure 9.

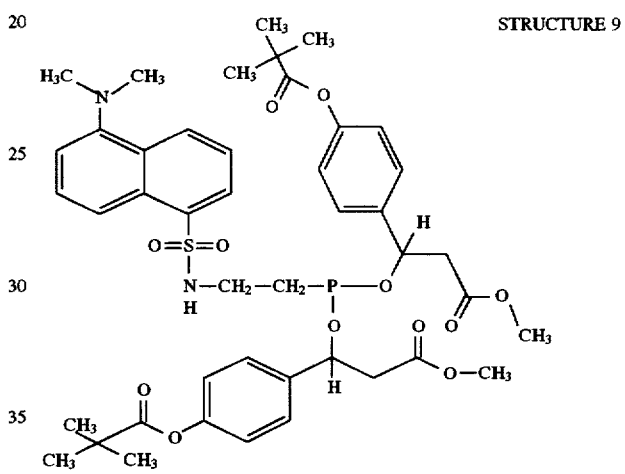

STRUCTURE 9

Synthesis of Compound Given by Structure 9

Four hundred and fifty mg of the dansyl phosphonate given by Structure 8 was refluxed under argon with 8 ml of 1,1,dichloromethyl ether (Aldrich) for 1 hour and allowed to sit at room temperature overnight. The ether was then decanted and 50 ml×3 of anhydrous toluene was added and removed exvacuo to yield a yellow crystalline product. 220 mg of this product was then reacted with 327 mg of methyl 3-hydroxy-3-(4-pivaloyloxyphenyl) propionate, 238 microliters of triethylamine, and 135 microliters of N-methylimidazole, in 2.0 ml of anhydrous CH$_2$Cl$_2$, under argon at room temperature. After 8 hours the solvent was removed exvacuo. The residue was dissolved in methylene chloride, washed with saline and dried. The product was then purified by on a Rainin C-18 Dynamax 60A preparative HPLC column at a flow rate of 10 ml/min. with an acetonitrile: water gradient. Three peaks were evident, in 2 collected fractions. Proton and phosphorus NMR were in agreement with the peaks being the expected diastereomers of structure 9. Mass spect. 882.3173 and 882.3182 with calculated mass of 882.3162.

Figure 8A:
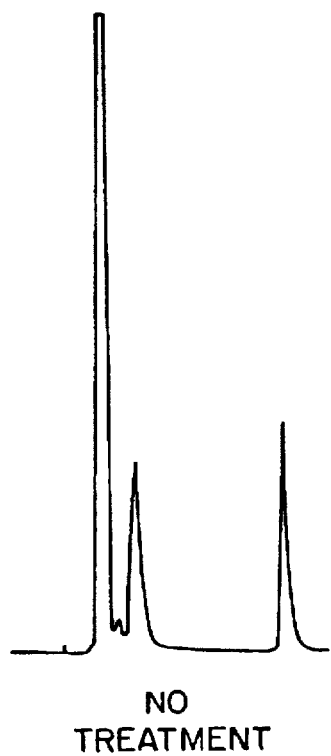
FIG. 8 is an illustration of high pressure liquid chromatograms of mouse kidney samples employing fluorescent detection. Shown are results from a normal mouse, a mouse treated with the dansyl phosphonate (Structure 8), and a mouse treated with the dansyl phosphonate prodrug (Structure 9). Dramatically increased levels of the dansyl phosphonate are present in the prodrug treated kidney.
Figure 8B:
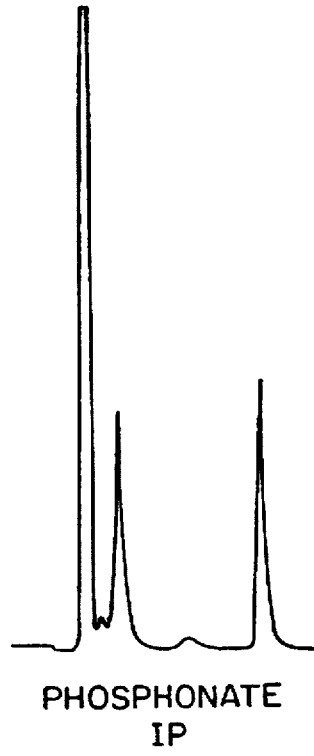
Figure 8C:
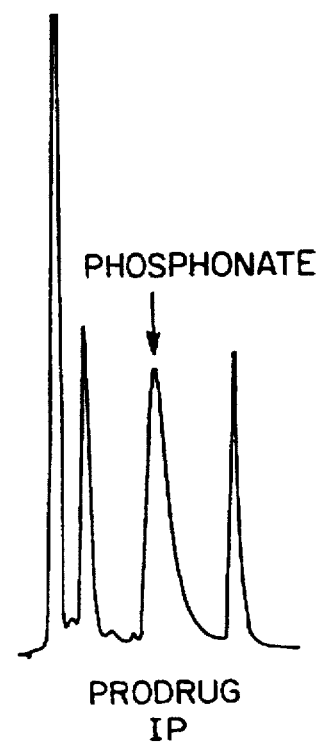

Metabolism Of The Dansyl Phosphonate Prodrug (Structure 9) BY Mice 6 week old CD-1 male mice were injected intraperitoneally (IP) with 0.5 ml of a 20% aqueous emulsion of Emulphor-EL620 (Rhoune-Poulec) containing 100 microliters/ml of dimethylsulfoxide and 5.5 mg/ml of a mixture of the 3 diastereomers given by Structure 9. Other mice received an equimolar amount of the dansyl phosphonic acid (Structure 8) in the same vehicle. The mice were sacrificed after 3.5 hours. Examination of the peritoneal cavity with an ultraviolet light revealed fluorescence concentrated in the mesenteric lymphatics in prodrug treated mice. Blood, liver, spleen and kidney samples were collected, immediately frozen, and stored overnight. The tissue samples were then thawed, rinsed with saline and weighed. Then a solution of 80% methanol containing 0.01M tetraoctlyammonium bromide and 20% 0.0005M aqueous Tris buffer at pH 7.98 was added and the samples were homogenized. The homogenate was then centrifuged and the supernatant was then subjected to ultrafiltration using centrifuge filtration tubes with cellulose membrane with a nominal molecular weight cut off of 5000. The ultrafiltrate was then analyzed by HPLC with fluorescent detection using an excitation wavelength of 228 nm and an emission wavelength of 518 nm. Dansyl derivatives are highly fluorescent in organic solvents but much less so in water. Accordingly, we employed reversed phase ion pair chromatography using 87.5% methanol, 0.01M tetraoctlyammonium bromide, and 12.5% 0.0005M aqueous Tris buffer at pH 7.98 at a flow rate of 0.9 ml/min with a Rainin C-18 Microsorb 3 micron, 10 cm analytical column. Under these conditions the dansyl phosphonic acid given by Structure 8 had a retention time of 6 minutes. In control mouse samples no fluorescent peaks were present in this region. Mice injected with the prodrug (Structure 9) had large amounts of fluorescent material detectable in the liver including a peak which corresponded to the dansyl phosphonate (Structure 8) and a peak at 4.0 which has the same retention time as a diastereomer of the prodrug (Structure 9). This was confirmed by experiments in which the samples were spiked with authentic prodrug or phosphonate. The levels of dansyl phosphonate in all tissues of prodrug treated mice was much higher then that observed in mice injected with an equal amount of the phosphonate. Highest levels were observed in the liver. Dansyl phosphonate was not detectable in the spleens of mice treated with the phosphonate (Structure 8) but readily detectable in the spleens of prodrug treated mice. These results demonstrate the enhanced delivery in vivo of a phosphonate using the prodrug approach. Representative chromatograms of liver, kidney, and spleen homogenates from a normal mouse, a mouse given dansyl phosphonate IP, and a mouse given the prodrug IP are shown in FIG. 7–9.

Equivalents

Those skilled in the arts will recognize or be able to ascertain, using no more than routine experimentation, many equivalents to the specific materials and components described herein. Such equivalents are intended to be encompassed in the scope of the following claims

I claim:
1. A compound represented by the following structural formula:

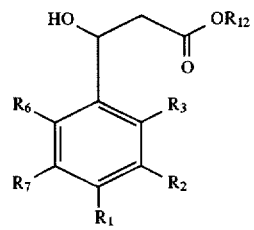

wherein:

$R_1$ is a ($-OCOR_{14}$) group; a ($-O-CO-O-R_{14}$) group; a ($-O-CO-NHCH_3$) group; or a ($-O-CO-N(CH_3)_2$) group;

$R_2$ and $R_7$ are independently hydrogen, a ($-CO_2R_{10}$) group; a methyl group; a halogen; a methoxy group; a ($-O-CO-R_8$) group, or a hydroxymethyl group ($HO-CH_2-$);

$R_3$ and $R_6$ are independently hydrogen; a methyl group, a hydroxymethyl group ($-CH_2-OH$); $-COOR_9$; a halogen; a hydroxyethyl group ($-CH_2-CH_2-OH$); $-CH_2CO_2R_{11}$; or $-CF_3$;

$R_8$ is a C1 to C31 straight chained alkyl group, isopropyl, t-butyl, a phenyl group or a group such that ($H-O-CO-R_8$) is an amino acid, lactic acid, glycolic acid, acetoacetic acid;

$R_9$, $R_{10}$, $R_{11}$ and $R_{12}$ are independently a methyl, ethyl, phenyl or benzyl group;

$R_{14}$ is a C1–C31 straight chain alkyl group, $-O-$(C1–C31 straight chain group), isopropyl, $-O$-isopropyl, t-butyl, $-O-$(t-butyl), phenyl, $-O$-phenyl, $-NHCH_3$, $-N(CH_3)_2$ or $R_{14}$ can be selected such that $R_{14}-CO_2H$ is an amino acid; lactic acid; glycolic acid ($-HO-CH_2-CO_2H$); glyceric acid ($HO-CH_2-CH(OH)-CO_2H$); or acetoacetic acid ($CH_3COCH_2-CO_2H$).

2. A compound of claim 1 of the following structure:

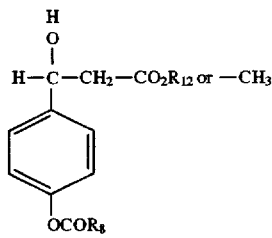

wherein $R_{12}$ is methyl or ethyl and $R_8$ is methyl or t-butyl.

3. A compound represented by the following structural formula:

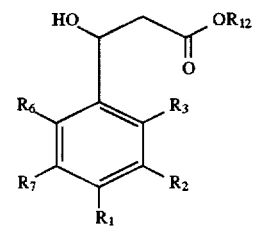

wherein:

$R_1$ is a ($-OCOR_{14}$) group; a ($-O-CO-O-R_{14}$) group; a ($-O-CO-NHCH_3$) group; or a ($-O-CO-N(CH_3)_2$) group;

$R_2$ and $R_7$ are independently hydrogen; a ($-CO_2R_{10}$) group; a C1—C31 straight chained alkyl group; isopropyl; t-butyl; a halogen; —O—(C1–C31 straight chained alkyl group); —O—(isopropyl); —O—(t-butyl); a ($-O-CO-R_8$) group; or a hydroxymethyl group ($HO-CH_2$);

$R_3$ and $R_6$ are independently hydrogen; a C1–C31 straight chained alkyl group; isopropyl; t-butyl; a ($-CO_2R_9$) group; a hydroxymethyl group ($-CH_2-OH$); a halogen; a hydroxyethyl group ($-CH_2-CH_2-OH$); a $-CH_2CO_2R_{11}$ group; or $-CF_3$;

$R_8$ is a C1–C31 straight chain alkyl group, isopropyl or t-butyl; a substituted or unsubstituted phenyl group, or a group such that ($H-O-CO-R_8$) is an amino acid, lactic acid, glycolic acid, acetoacetic acid;

$R_9$, $R_{10}$, $R_{11}$ and $R_{12}$ are independently a C1–C30 straight chain alkyl group, an isopropyl group or a t-butyl group; a phenyl group, a substituted phenyl group, a benzyl group or a substituted benzyl group;

$R_{14}$ is a C1–C31 straight chain alkyl group, —O—(C1–C31 straight chain group), isopropyl, —O-isopropyl, t-butyl, —O—(t-butyl), phenyl, —O-phenyl, a substituted phenyl group, —O—(substituted phenyl), —NHCH$_3$, —N(CH$_3$)$_2$ or $R_{14}$ can be selected such that $R_{14}-CO_2H$ is; an amino acid; lactic acid; glycolic acid ($-HO-CH_2-CO_2H$); glyceric acid ($HO-CH_2-CH(OH)-CO_2H$); or acetoacetic acid ($CH_3COCH_2-CO_2H$).

* * * * *